US012209062B2

United States Patent
Takata et al.

(10) Patent No.: US 12,209,062 B2
(45) Date of Patent: Jan. 28, 2025

(54) NITRILE OXIDE COMPOUND

(71) Applicants: TOKYO INSTITUTE OF TECHNOLOGY, Tokyo (JP); DAIKIN INDUSTRIES, LTD., Osaka (JP)

(72) Inventors: Toshikazu Takata, Tokyo (JP); Hiromitsu Sogawa, Tokyo (JP); Tadashi Kanbara, Osaka (JP); Tsuyoshi Noguchi, Osaka (JP)

(73) Assignees: TOKYO INSTITUTE OF TECHNOLOGY, Tokyo (JP); DAIKIN INDUSTRIES, LTD., Osaka (JP)

( * ) Notice: Subject to any disclaimer, the term of this patent is extended or adjusted under 35 U.S.C. 154(b) by 623 days.

(21) Appl. No.: 17/104,957

(22) Filed: Nov. 25, 2020

(65) Prior Publication Data

US 2021/0078944 A1    Mar. 18, 2021

Related U.S. Application Data

(63) Continuation of application No. PCT/JP2019/020910, filed on May 27, 2019.

(30) Foreign Application Priority Data

May 28, 2018    (JP) .................. 2018-101616

(51) Int. Cl.
| | | |
|---|---|---|
| C07C 291/06 | (2006.01) | |
| C03C 17/28 | (2006.01) | |
| C07C 205/31 | (2006.01) | |
| C07C 255/64 | (2006.01) | |
| C07C 323/03 | (2006.01) | |
| C07C 323/47 | (2006.01) | |
| C07C 331/20 | (2006.01) | |
| C09D 5/00 | (2006.01) | |

(52) U.S. Cl.
CPC ............ *C07C 291/06* (2013.01); *C03C 17/28* (2013.01); *C07C 205/31* (2013.01); *C07C 255/64* (2013.01); *C07C 323/03* (2013.01); *C07C 323/47* (2013.01); *C07C 331/20* (2013.01); *C09D 5/00* (2013.01); *C03C 2217/76* (2013.01)

(58) Field of Classification Search
CPC .................................................. C07C 291/06
See application file for complete search history.

(56) References Cited

U.S. PATENT DOCUMENTS

| | | | | |
|---|---|---|---|---|
| 9,518,009 | B2 * | 12/2016 | Kanbara | ............... C07C 291/06 |
| 10,633,333 | B2 * | 4/2020 | Kanbara | ............... C08G 65/007 |
| 2011/0054134 | A1 | 3/2011 | Seo et al. | |
| 2015/0251995 | A1 | 9/2015 | Kanbara et al. | |
| 2016/0002153 | A1 * | 1/2016 | Kanbara | ............... C07C 291/06 |
| | | | | 525/331.7 |
| 2018/0057450 | A1 * | 3/2018 | Kanbara | .................. C07F 9/40 |

FOREIGN PATENT DOCUMENTS

| | | |
|---|---|---|
| JP | 2011-052072 A | 3/2011 |
| JP | 2013-112741 A | 6/2013 |
| WO | 2014/136952 A1 | 12/2014 |
| WO | WO-2016143869 A1 * | 9/2016 ........... C07C 291/06 |

OTHER PUBLICATIONS

STN International, File Registry [online], published on Mar. 7, 2016, retrieved on Jul. 23, 2019, CAS registration No. 1880782-84-2.

Hiromitsu Sogawa et al., "Modification of rubber and surface under non-catalytic and solvent-free conditions using fluorine-containing nitrile oxide", Abstracts of the Elastomer Symposium, Dec. 4, 2014, 26th, (7 pages total).

Extended European Search Report dated May 2, 2022 for related European Application No. 19811486.0.

International Search Report for PCT/JP2019/020910 dated Aug. 6, 2019 (PCT/ISA/210).

International Preliminary Report on Patentability (with translation of Written Opinion) dated Dec. 1, 2020, issued by the International Bureau in application No. PCT/JP2019/020910.

\* cited by examiner

*Primary Examiner* — Matthew P Coughlin
(74) *Attorney, Agent, or Firm* — Sughrue Mion, PLLC

(57) ABSTRACT

The present invention provides a compound represented by formula (I) wherein symbols in the formula are as defined in the specification.

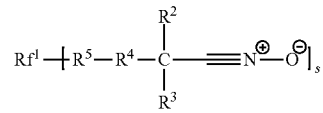

7 Claims, No Drawings

NITRILE OXIDE COMPOUND

This is a Continuation Application under 37 C.F.R. § 1.53(b) of International Application No. PCT/JP2019/020910 filed May 27, 2019, which claims priority from Japanese Patent Application No. 2018-101616 filed May 28, 2018. The above noted applications are incorporated herein by reference in their respective entireties.

TECHNICAL FIELD

The present invention relates to a nitrile oxide compound, a production method therefor, and a composition comprising the compound.

BACKGROUND ART

Compounds having a nitrile oxide group readily undergo a click reaction ([2+3] addition cyclization reaction) with an unsaturated bond in another compound, and are thus known to be useful as reacting agents in various applications. However, nitrile oxide compounds likely undergo reactions such as dimerization and are thus problematic by being significantly unstable.

Concerning this problem, it is known that a relatively stable nitrile oxide compound can be obtained by forming an aromatic nitrile oxide compound having a substituent at the ortho-position (Patent Literature 1).

Also, it is known that a stable nitrile oxide compound can be obtained by forming an aliphatic nitrile oxide compound that has a bulky substituent on carbon at the α-position of the nitrile oxide group (Patent Literatures 2 and 3).

CITATION LIST

Patent Literature

Patent Literature 1 Japanese Patent Laid-Open No. 2011-052072
Patent Literature 2 International Publication No. WO 2014/136952
Patent Literature 3 Japanese Patent Laid-Open No. 2013-112741

SUMMARY OF THE INVENTION

Problems to be Solved by the Invention

However, conventional nitrile oxide compounds have limited structures due to the difficulty of synthesis. In particular, when it is desired to impart oil-repellency to a base material by a nitrile oxide compound, a nitrile oxide compound having a substituent that contains a fluoroalkyl group or a fluoropolyether group is considered effective, but there has been no report of synthesizing a nitrile oxide compound in which a substituent containing a fluoroalkyl group or a fluoropolyether group is bonded via a heteroatom to the carbon atom to which the nitrile oxide group is bonded.

An object of the present disclosure is to provide a nitrile oxide compound which is capable of imparting oil-repellency to a base material and in which a substituent containing a fluoroalkyl group or a fluoropolyether group is bonded via a heteroatom to the carbon atom to which the nitrile oxide group is bonded.

Means to Solve the Problem

The present invention includes the following embodiments.

[1] A compound represented by formula (I):

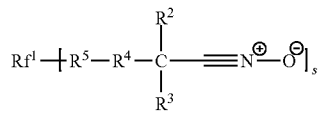

wherein
$Rf^1$ is a fluoroalkyl group, a fluoroalkylene group, or a monovalent or divalent fluoropolyether group;
$R^2$ and $R^3$ are each independently at each occurrence a hydrogen atom or a hydrocarbon group;
$R^4$ is each independently at each occurrence —O—, —S—, —NR$^7$—, or —O—P(=O)(OR$^8$)—;
$R^5$ is each independently at each occurrence a divalent hydrocarbon group having two or more carbon atoms in the main chain;
$R^7$ is each independently at each occurrence a hydrogen atom or a hydrocarbon group;
$R^8$ is each independently at each occurrence a hydrocarbon group; and
s is 1 or 2.

[2] The compound according to [1], wherein $Rf^1$ is a perfluoroalkyl group, a perfluoroalkylene group, or a monovalent or divalent perfluoropolyether group.

[3] The compound according to [1] or [2], wherein $R^4$ is each independently at each occurrence —O— or —S—.

[4] The compound according to any one of [1] to [3], wherein $R^5$ is each independently at each occurrence:

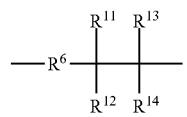

wherein
$R^6$ is a single bond or a divalent organic group;
$R^{11}$ is a hydrogen atom or an alkyl group having 1 to 6 carbon atoms;
$R^{12}$ is a hydrogen atom or an alkyl group having 1 to 6 carbon atoms;
$R^{13}$ is a hydrogen atom or an alkyl group having 1 to 6 carbon atoms; and
$R^{14}$ is a hydrogen atom or an alkyl group having 1 to 6 carbon atoms.

[5] The compound according to [4], wherein $R^6$ is a single bond, an alkylene group, or an alkyleneoxy group.

[6] A compound represented by formula (II):

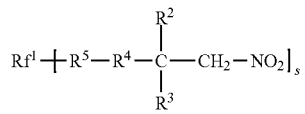

wherein
$Rf^1$ is a fluoroalkyl group, a fluoroalkylene group, or a monovalent or divalent fluoropolyether group;
$R^2$ and $R^3$ each independently at each occurrence is a hydrogen atom or a hydrocarbon group;
$R^4$ is each independently at each occurrence —O—, —S—, —NR$^7$—, or —O—P(=O)(OR$^8$)—;

$R^5$ is each independently at each occurrence a divalent hydrocarbon group having two or more carbon atoms in the main chain;

$R^7$ is each independently at each occurrence a hydrogen atom or a hydrocarbon group;

$R^8$ is each independently at each occurrence a hydrocarbon group; and s is 1 or 2.

[7] A composition comprising one or more compounds according to any one of [1] to [5] for being applied to a material comprising a group having reactivity with a nitrile oxide group.

Effect of the Invention

The present invention can provide a nitrile oxide compound in which a substituent containing a fluoroalkyl group or a fluoropolyether group is bonded via a heteroatom to the carbon atom to which the nitrile oxide group is bonded.

EMBODIMENTS TO CARRY OUT THE INVENTION

Herein, the "hydrocarbon group" means a group containing a carbon atom and a hydrogen atom unless stated otherwise (provided that the hydrogen atom may be partially or fully replaced with a substituent described below). The "hydrocarbon group" is not limited, and examples include $C_{1-20}$ hydrocarbon groups, such as aliphatic hydrocarbon groups and aromatic hydrocarbon groups, that are optionally substituted with one or more substituents. The hydrocarbon group may have one or more N, O, S, and like atoms at the terminal or within the molecular chain.

Herein, the "aliphatic hydrocarbon group" may be linear, branched, or cyclic, may be saturated or unsaturated, and may contain one or more ring structures, unless stated otherwise. The "aliphatic hydrocarbon group" is not limited, and examples include an alkyl group, an alkenyl group, an alkynyl group, a cycloalkyl group, and a cycloalkenyl group. The "aliphatic hydrocarbon group" may be substituted with one or more substituents.

Herein, the "alkyl group" may be linear or branched unless stated otherwise, for example, an alkyl group having 1 to 20, preferably 1 to 12, and more preferably 1 to 6 carbon atoms. The "alkyl group" is not limited, and examples include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethyl propyl group, a n-hexyl group, a 1-methylpentyl group, a 2-methylpentyl group, a 3-methylpentyl group, a 4-methylpentyl group, a n-hexyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1,2,2-trimethylpropyl group, a 1-ethyl-l-methylpropyl group, and a 1-ethyl-2-methylpropyl group. The "alkyl group" may be substituted with one or more substituents.

Herein, the "alkenyl group" may be linear or branched unless stated otherwise, and is, for example, an alkenyl group having 2 to 20, preferably 2 to 12, and more preferably 2 to 6 carbon atoms. The "alkenyl group" is not limited and may be obtained by, for example, replacing at least one carbon-carbon single bond of the above alkyl group with a carbon-carbon double bond, and specific examples include a vinyl group, an allyl group, a 1-propenyl group, an isopropenyl group, a 2-methyl-1-propenyl group, a 2-methyl-2-propenyl group, a 1-butenyl group, a 2-butenyl group, a 3-butenyl group, a 1-pentenyl group, a 1-hexenyl group, a 1,3-hexadienyl group, and a 1,5-hexadienyl group. The "alkenyl group" may be substituted with one or more substituents.

Herein, the "alkynyl group" may be linear or branched unless stated otherwise, and is, for example, an alkynyl group having 2 to 20, preferably 2 to 12, and more preferably 2 to 6 carbon atoms. The "alkynyl group" is not limited and may be obtained by, for example, replacing at least one carbon-carbon single bond of the above alkyl group with a carbon-carbon triple bond, and specific examples include an ethynyl group, a 1-propynyl group, a 2-propynyl group, a 1-butynyl group, a 2-butynyl group, a 3-butynyl group, a 1-methyl-2-propynyl group, a 1-pentynyl group, a 1-ethyl-2-propynyl group, a 1-hexynyl group, and a 2-hexynyl group. The "alkynyl group" may be substituted with one or more substituents.

Herein, the "cycloalkyl group" is a cyclic alkyl group having 3 to 20 and preferably 5 to 12 carbon atoms unless stated otherwise. The "cycloalkyl group" is not limited, and examples include a cyclopropyl group, a cyclobutyl group, a cyclopentyl group, a cyclohexyl group, a cycloheptyl group, and a cyclooctyl group. The "cycloalkyl group" may be substituted with one or more substituents.

Herein, the "cycloalkenyl group" is a cyclic alkenyl group having 3 to 20 and preferably 5 to 12 carbon atoms unless stated otherwise. The "cycloalkenyl group" is not limited, and examples include a cyclopropenyl group, a cyclobutenyl group, a cyclopentenyl group, a cyclohexenyl group, a cycloheptenyl group, and a cyclooctenyl group. The "cycloalkenyl group" may be substituted with one or more substituents.

Herein, the "aromatic hydrocarbon group (hereinafter also referred to as an aryl group)" may be monocyclic or polycyclic such as bicyclic or tricyclic, or may be an aromatic heterocyclic group (hereinafter also referred to as a heteroaryl group), unless stated otherwise. The "aromatic hydrocarbon group" is not limited, and examples include aryl groups having 3 to 20 carbon atoms such as a phenyl group and a naphthyl group, and heteroaryl groups having 3 to 20 carbon atoms such as a furyl group, a thienyl group, a pyridyl group, an indolyl group, a quinolyl group, an isoquinolyl group, and an imidazolyl group. The "aromatic hydrocarbon group" may be substituted with one or more substituents.

Herein, the "alkylene group" means a divalent group obtained by removing one hydrogen atom on a carbon atom of the above alkyl group unless stated otherwise.

Herein, the "(poly)alkyl ether group" means a group in which an ethereal oxygen atom is introduced in one or more carbon-carbon bonds of the above alkyl group unless stated otherwise.

Herein, the above hydrocarbon group, alkyl group, alkenyl group, alkynyl group, cycloalkyl group, cycloalkenyl group, aromatic hydrocarbon group, and alkylene group may be substituted unless stated otherwise. The substituent is not limited, and examples include an oxygen atom; a halogen atom (fluorine, chlorine, bromine, iodine); a hydroxyl group; an unsubstituted, mono-, or di-substituted amino group; a nitro group; an azido group; a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group, a $C_{6-16}$ heteroaryl group, a $C_{1-16}$ alkoxy group, $C_{6-16}$ aryloxy, $C_{1-16}$ alkylthio, and $C_{1-20}$ (poly)alkyl ether group that are optionally substituted with one or more halogen atoms; and —O—C(O)—OR$^a$, —O—C(O)—NR$^a_2$, —C(O)—R$^a$, —C(O)—OR$^a$, —NR$^a$—C(O)—R$^a$, —NR$^a$—C(NR$^a$)—R$^a$, —C(NR$^a$)—R$^a$, and —C(NR$^a$)—NR$^a_2$ (wherein R$^a$ each independently represents a hydrogen atom, a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group, or a $C_{6-16}$ heteroaryl group).

The "monosubstituted amino group" is not limited, and each means an amino group substituted with one substituent independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group, and a $C_{6-16}$ heteroaryl group. The "monosubstituted amino group" is not limited, and examples include methylamino, ethylamino, and phenylamino.

The "disubstituted amino group" is not limited, and means an amino group substituted with two substituents independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group, and a $C_{6-16}$ heteroaryl group. The "disubstituted amino group" is not limited, and examples include dimethylamino, diethylamino, and diphenylamino.

The "$C_{1-16}$ alkoxy group" is not limited, and examples include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a neopentyloxy group, a tert-pentyloxy group, a 1-ethylpropoxy group, a n-hexyloxy group, an isohexyloxy group, a neohexyloxy group, and a 2-ethylbutoxy group.

The "$C_{6-16}$ aryloxy" is not limited, and examples include phenoxy and naphthyloxy.

The "$C_{1-16}$ alkylthio" is not limited, and examples include methylthio, ethylthio, propylthio, isopropylthio, butylthio, sec-butylthio, and tert-butylthio.

Herein, the "halogen (or the halogen atom)" means a fluorine atom, a chlorine atom, a bromine atom, an iodine atom, or the like unless stated otherwise.

Below, the compound of the present disclosure will now be described.

The present disclosure provides a compound represented by formula (I) (hereinafter also referred to as the "compound (I) of the present disclosure"):

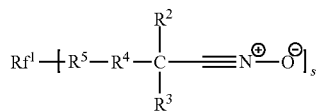

wherein
Rf$^1$ is a fluoroalkyl group, a fluoroalkylene group, or a monovalent or divalent fluoropolyether group;
R$^2$ and R$^3$ each independently at each occurrence represent a hydrogen atom or a hydrocarbon group;
R$^4$ is each independently at each occurrence —O—, —S—, —NR$^7$—, or —O—P(=O)OR$^8$—;

R$^5$ is each independently at each occurrence a divalent hydrocarbon group having two or more carbon atoms in the main chain;
R$^7$ is each independently at each occurrence a hydrogen atom or a hydrocarbon group;
R$^8$ is each independently at each occurrence a hydrocarbon group; and
s is 1 or 2.

In formula (I), Rf$^1$ is a fluoroalkyl group, a fluoroalkylene group, or a monovalent or divalent fluoropolyether group. The carbon atom of Rf$^1$, which is bonded to R$^5$, preferably has at least one fluorine atom.

The fluoroalkyl group represents an alkyl group substituted with one or more fluorine atoms. The fluoroalkyl group may be preferably an alkyl group having 1 to 20 carbon atoms, more preferably an alkyl group having 4 to 20 carbon atoms, and even more preferably an alkyl group having 6 to 16 carbon atoms, and substituted with one or more fluorine atoms. The fluoroalkyl group may be linear or branched, and is preferably linear.

The fluoroalkyl group is preferably a linear or branched perfluoroalkyl group, and is preferably a linear perfluoroalkyl group. The perfluoroalkyl group is preferably a perfluoroalkyl group having 1 to 20 carbon atoms, more preferably a perfluoroalkyl group having 4 to 20 carbon atoms, and even more preferably a perfluoroalkyl group having 6 to 16 carbon atoms.

The fluoroalkylene group is a divalent group obtained by removing one hydrogen atom or fluorine atom from the above fluoroalkyl group.

The monovalent and divalent fluoropolyether groups are groups represented by the following formulas (a) and (b), respectively:

wherein
Rf$^2$ is a $C_{1-16}$ alkyl group optionally substituted with one or more fluorine atoms;
Rf$^3$ is a $C_{1-6}$ alkylene group optionally substituted with one or more fluorine atoms;
p1 is 0 or 1;
q1 is each independently at each occurrence 0 or 1; and
PFPE is a group represented by the formula:

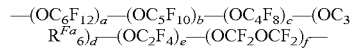

wherein
R$^{Fa}$ is each independently at each occurrence a hydrogen atom, a fluorine atom, or a chlorine atom; and
a, b, c, d, e, and f are each independently an integer of 0 or more and 200 or less, the sum of a, b, c, d, e, and f is at least 1, and the occurrence order of each repeating unit enclosed within parentheses provided with a, b, c, d, e, or f is arbitrary in the formula.

In one embodiment, the monovalent and divalent fluoropolyether groups are groups represented by the following formulas (a) and (b), respectively:

wherein
Rf$^2$ is a $C_{1-16}$ alkyl group optionally substituted with one or more fluorine atoms; and PFPE is a group represented by the formula:

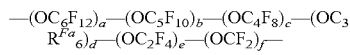

wherein $R^{Fa}$ is each independently at each occurrence a hydrogen atom, a fluorine atom, or a chlorine atom; and a, b, c, d, e, and f are each independently an integer of 0 or more and 200 or less, the sum of a, b, c, d, e, and f is at least 1, and the occurrence order of each repeating unit enclosed within parentheses provided with a, b, c, d, e, or f is arbitrary in the formula.

The "$C_{1-16}$ alkyl group" in the $C_{1-16}$ alkyl group optionally substituted with one or more fluorine atoms may be linear or branched, and is preferably a linear or branched alkyl group having 1 to 6 carbon atoms and in particular 1 to 3 carbon atoms, and is more preferably a linear alkyl group having 1 to 3 carbon atoms.

$Rf^2$ is preferably a $C_{1-16}$ alkyl group substituted with one or more fluorine atoms, more preferably a $CF_2H$—$C_{1-15}$ fluoroalkylene group, and even more preferably a $C_{1-16}$ perfluoroalkyl group.

The $C_{1-16}$ perfluoroalkyl group may be linear or branched, and is preferably a linear or branched perfluoroalkyl group having 1 to 6 carbon atoms and in particular 1 to 3 carbon atoms, is more preferably a linear perfluoroalkyl group having 1 to 3 carbon atoms, and is specifically —$CF_3$, —$CF_2CF_3$, or —$CF_2CF_2CF_3$.

$R^{Fa}$ is preferably a hydrogen atom or a fluorine atom, and is more preferably a fluorine atom.

PFPE is preferably a group represented by the formula:

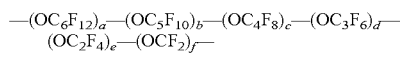

The above a, b, c, d, e, and f are each independently an integer of 0 or more and 200 or less, and the sum of a, b, c, d, e, and f is at least 1. Preferably, the sum of a, b, c, d, e, and f is 5 or more, and more preferably 10 or more. Preferably, the sum of a, b, c, d, e, and f is 300 or less and more preferably 200 or less, such as 10 or more and 200 or less and more specifically 10 or more and 100 or less.

The above a and b are preferably each independently 0 or more and 30 or less, and may be 0.

In one embodiment, a, b, c, and d are each independently preferably an integer of 0 or more and 30 or less, more preferably an integer of 20 or less, particularly preferably an integer of 10 or less, and even more preferably an integer of 5 or less, and may be 0.

In one embodiment, the sum of a, b, c, and d is preferably 30 or less, more preferably 20 or less, even more preferably 10 or less, and particularly preferably 5 or less.

In one embodiment, the sum of e and f is preferably 30 or more, more preferably 40 or more, and even more preferably 50 or more.

These repeating units may be linear or branched. For example, —$(OC_6F_{12})$— may be —$(OCF_2CF_2CF_2CF_2CF_2CF_2)$—, —$(OCF(CF_3)CF_2CF_2CF_2CF_2)$—, —$(OCF_2CF(CF_3)CF_2CF_2CF_2)$—, —$(OCF_2CF_2CF(CF_3)CF_2CF_2)$—, —$(OCF_2CF_2CF_2CF(CF_3)CF_2)$—, —$(OCF_2CF_2CF_2CF_2CF(CF_3))$—, or the like, and is preferably —$(OCF_2CF_2CF_2CF_2CF_2CF_2)$—. —$(OC_5F_{10})$— may be —$(OCF_2CF_2CF_2CF_2CF_2)$—, —$(OCF(CF_3)CF_2CF_2CF_2)$—, —$(OCF_2CF(CF_3)CF_2CF_2)$—, —$(OCF_2CF_2CF(CF_3)CF_2)$—, —$(OCF_2CF_2CF_2CF(CF_3))$, or the like, and is preferably —$(OCF_2CF_2CF_2CF_2CF_2)$—. —$(OC_4F_8)$— may be any of —$(OCF_2CF_2CF_2CF_2)$—, —$(OCF(CF_3)CF_2CF_2)$—, —$(OCF_2CF(CF_3)CF_2)$—, —$(OCF_2CF_2CF(CF_3))$—, —$(OC(CF_3)_2CF_2)$—, —$(OCF_2C(CF_3)_2)$—, —$(OCF(CF_3)CF(CF_3))$—, —$(OCF(C_2F_5)CF_2)$—, and —$(OCF_2CF(C_2F_5))$— and is preferably —$(OCF_2CF_2CF_2CF_2)$—. —$(OC_3F_6)$— may be any of —$(OCF_2CF_2CF_2)$—, —$(OCF(CF_3)CF_2)$—, and —$(OCF_2CF(CF_3))$—, and is preferably —$(OCF_2CF_2CF_2)$—. —$(OC_2F_4)$— may be any of —$(OCF_2CF_2)$— and —$(OCF(CF_3))$—, and is preferably —$(OCF_2CF_2)$—.

In one embodiment, the above repeating units are linear. By making the repeating units linear, the surface-treating layer has an increased lubricity when the compound (I) of the present disclosure is used as a surface-treating agent.

In another embodiment, the repeating units are branched. By making the repeating units branched, the dynamic friction coefficient of the surface-treating layer can be increased when the compound (I) of the present disclosure is used as a surface-treating agent.

In one embodiment, PFPE is —$(OC_3F_6)_d$— wherein d is an integer of 1 or more and 200 or less, preferably 5 or more and 200 or less, and more preferably 10 or more and 200 or less. Preferably, PFPE is —$(OCF_2CF_2CF_2)_d$— wherein d is an integer of 1 or more and 200 or less, preferably 5 or more and 200 or less, and more preferably 10 or more and 200 or less, or —$(OCF(CF_3)CF_2)_d$— wherein d is an integer of 1 or more and 200 or less, preferably 5 or more and 200 or less, and more preferably 10 or more and 200 or less. More preferably, PFPE is —$(OCF_2CF_2CF_2)_d$— wherein d is an integer of 1 or more and 200 or less, preferably 5 or more and 200 or less, and more preferably 10 or more and 200 or less.

In another embodiment, PFPE is —$(OC_4F_8)_c$—$(OC_3F_6)_d$—$(OC_2F_4)_e$—$(OCF_2)_f$— wherein c and d are each independently an integer of 0 or more and 30 or less, e and f are each independently an integer of 1 or more and 200 or less, preferably 5 or more and 200 or less, and more preferably 10 or more and 200 or less, the sum of c, d, e, and f is at least 5 and more preferably 10 or more, and the occurrence order of each repeating unit enclosed within parentheses provided with c, d, e, or f is arbitrary in the formula. Preferably, PFPE is —$(OCF_2CF_2CF_2CF_2)_c$—$(OCF_2CF_2CF_2)_d$—$(OCF_2CF_2)_e$—$(OCF_2)_f$—.

In one embodiment, PFPE is —$(OC_2F_4)_e$—$(OCF_2)_f$— wherein e and f are each independently an integer of 1 or more and 200 or less, preferably 5 or more and 200 or less, and more preferably 10 or more and 200 or less, and the occurrence order of each repeating unit enclosed within parentheses provided with e or f is arbitrary in the formula.

In yet another embodiment, PFPE is a group represented by —$(R^{26}—R^{27})_g$—. In the formula, $R^{26}$ is $OCF_2$ or $OC_2F_4$, and preferably $OC_2F_4$. In the formula, $R^{27}$ is a group selected from $OC_2F_4$, $OC_3F_6$, $OC_4F_8$, $OC_5F_{10}$, and $OC_6F_{12}$, or is a combination of 2 or 3 groups independently selected from these groups. Preferably, $R^{27}$ is a group selected from $OC_2F_4$, $OC_3F_6$, and $OC_4F_8$, or a group selected from $OC_3F_6$, $OC_4F_8$, $OC_5F_{10}$, and $OC_6F_{12}$, or a combination of 2 or 3 groups independently selected from these groups. The combination of 2 or 3 groups independently selected from $OC_2F_4$, $OC_3F_6$, and $OC_4F_8$ is not limited, and examples include —$OC_2F_4OC_3F_6$—, —$OC_2F_4OC_4F_8$—, —$OC_3F_6OC_2F_4$—, —$OC_3F_6OC_3F_6$—, —$OC_3F_6OC_4F_8$—, —$OC_4F_8OC_4F_8$—, —$OC_4F_8OC_3F_6$—, —$OC_4F_8OC_2F_4$—, —$OC_2F_4OC_2F_4OC_3F_6$—, —$OC_2F_4OC_2F_4OC_4F_8$—, —$OC_2F_4OC_3F_6OC_2F_4$—, —$OC_2F_4OC_3F_6OC_3F_6$—, —$OC_2F_4OC_4F_8OC_2F_4$—, —$OC_3F_6OC_2F_4OC_2F_4$—, —$OC_3F_6OC_2F_4OC_3F_6$—, —$OC_3F_6$—$C_3F_6$—$C_2F_4$—, and —$OC_4F_8OC_2F_4OC_2F_4$—. The above g is an integer of 2 or more, preferably 3 or more and more preferably 5 or more, and 100 or less and preferably 50 or less. In the formula, $OC_2F_4$, $OC_3F_6$, $OC_4F_8$, $OC_5F_{10}$, and $OC_6F_{12}$ may be linear or branched, and are preferably linear. In this embodiment, PFPE is preferably $—(OC_2F_4—OC_3F_6)_g—$ or $—(OC_2F_4—OC_4F_8)_g—$.

In yet another embodiment, PFPE is a group represented by:

$—(OC_6F_{12})_a—(OC_5F_{10})_b—(OC_4F_8)_c—(OC_3F_6)_d—(OC_2F_6)_e—(OCF_2)_f—$ wherein e is an integer of 1 or more and 200 or less, a, b, c, d, and f are each independently an integer of 0 or more and 200 or less, the sum of a, b, c, d, e, and f is at least 1, and the occurrence order of each repeating unit enclosed within parentheses provided with a, b, c, d, e, or f is arbitrary in the formula. In one embodiment, e is preferably an integer of 1 or more and 100 or less, and more preferably 5 or more and 100 or less. The sum of a, b, c, d, e, and f is preferably 5 or more and more preferably 10 or more, and is, for example, 10 or more and 100 or less.

The number average molecular weight of PFPE is not limited, and is, for example, 500 to 30,000, preferably 1,500 to 30,000, and more preferably 2,000 to 10,000. The number average molecular weight is a value measured by $^{19}$F-NMR.

In formula (I), $R^2$ and $R^3$ each independently represent a hydrogen atom or a hydrocarbon group. The hydrocarbon group is not limited, and examples include an alkyl group, a cycloalkyl group, a heterocycloalkyl group, an aryl group, and a (poly)alkyl, optionally having one or more substituents.

In one embodiment, at least one of $R^2$ and $R^3$ is a hydrocarbon group, and preferably $R^2$ and $R^3$ are both hydrocarbon groups.

In one embodiment, at least one of $R^2$ and $R^3$ is an aryl group, a tert-alkyl group, a sec-alkyl group, or a (poly)alkyl, optionally substituted with one or more substituents.

In one embodiment, $R^2$ and $R^3$ each independently are preferably an alkyl group having 1 to 6 carbon atoms or an aryl group having 6 to 10 carbon atoms, more preferably a branched alkyl group having 3 to 6 carbon atoms or an aryl group having 6 to 10 carbon atoms, even more preferably a branched alkyl group having 3 to 6 carbon atoms or a phenyl group, and particularly preferably a tert-butyl group or a phenyl group.

In one embodiment, at least one of $R^2$ and $R^3$ is a fluoroalkyl group or a group (for example, an alkyl group, preferably a sec-alkyl group or a tert-alkyl group, or an aryl group, or preferably a phenyl group or an alkyl group) substituted with a fluoroalkyl group. Preferably, the fluoroalkyl group is a fluoroalkyl group in which the terminal carbon atom is $CF_2H—$, and hydrogen atoms on all other carbon atoms are entirely replaced with fluorine, or is a perfluoroalkyl group, and is more preferably a perfluoroalkyl group. Preferably, one or both of $R^2$ and $R^3$ are each independently an alkyl group substituted with a perfluoroalkyl group.

In one embodiment, at least one of $R^2$ and $R^3$ is a phenyl group having an alkoxy group that is substituted with a perfluoroalkyl group.

In formula (I), $R^4$ is $—O—$, $—S—$, $—NR^7—$, or $—O—P(=O)OR^8—$. $R^4$ is preferably $—O—$, $—S—$, or $—O—P(=O)OR^8—$, more preferably $—O—$ or $—S—$, and even more preferably $—O—$.

In formula (I), $R^7$ is each independently at each occurrence a hydrogen atom or a hydrocarbon group. $R^7$ may be each independently at each occurrence preferably a hydrogen atom or an alkyl group having 1 to 6 carbon atoms, more preferably a hydrogen atom or an alkyl group having 1 to 3 carbon atoms, and even more preferably a hydrogen atom or a methyl group.

$R^8$ is each independently at each occurrence a hydrocarbon group. $R^8$ may be each independently at each occurrence preferably an alkyl group having 1 to 6 carbon atoms, more preferably an alkyl group having 1 to 3 carbon atoms, and even more preferably a methyl group.

In formula (I), $R^5$ is each independently at each occurrence a divalent hydrocarbon group having two or more carbon atoms in the main chain. Here, the "main chain" in $R^5$ means a chain that connects $Rf^1$ and $R^4$ and that has the smallest number of atoms. By making $R^5$ have two or more carbon atoms in the main chain, introduction of a group having a nitrile oxide group into the $Rf^1—R^5—R^4$ group containing $Rf^1$ having a fluorine atom is become easy.

$R^5$ is understood as a linker connecting $Rf^1$ and $R^4$. Accordingly, $R^5$ may be any hydrocarbon group as long as it has two or more carbon atoms in the main chain, and the compound represented by formula (I) can stably exist.

Examples of $R^5$ are not limited, and include divalent groups represented by the following formula:

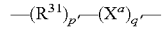

wherein $R^{31}$ represents a single bond, $—(CH_2)_{r'}—$, or an o-, m- or p-phenylene group and is preferably $—(CH_2)_{r'}—$, r' is an integer of 1 to 20, preferably an integer of 1 to 6, more preferably an integer of 1 to 3, and even more preferably 1 or 2, $X^a$ represents $—(X^b)_{l'}—$, $X^b$ each independently at each occurrence represents a group selected from the group consisting of $—O—$, $—S—$, an o-, m- or p-phenylene group, $—C(O)O—$, $—Si(R^{33})_2—$, $—(Si(R^{33})_2O)_{m'}—Si(R^{33})_2—$, $—CONR^{34}—$, $—O—CONR^{34}—$, $—NR^{34}—$, and $—(CH_2)_{n'}—$, $R^{33}$ each independently at each occurrence represents a phenyl group, a $C_{1-6}$ alkyl group, or a $C_{1-6}$ alkoxy group, and is preferably a phenyl group or a $C_{1-6}$ alkyl group, and more preferably a methyl group, $R^{34}$ each independently at each occurrence represents a hydrogen atom, a phenyl group, or a $C_{1-6}$ alkyl group (preferably a methyl group), m' is each independently at each occurrence an integer of 1 to 100, and preferably an integer of 1 to 20, n' is each independently at each occurrence an integer of 1 to 20, preferably an integer of 1 to 6, and more preferably an integer of 1 to 3, l' is an integer of 1 to 10, preferably an integer of 1 to 5, and more preferably an integer of 1 to 3, p' is 0 or 1, and q' is 0 or 1, provided that at least one of p' and q' is 1, and the occurrence order of each repeating unit enclosed within parentheses provided with p' or q' is arbitrary. Here, $R^{31}$ and $X^a$ (typically, hydrogen atoms of $R^{31}$ and $X^a$) may be substituted with one or more substituents selected from $C_{1-3}$ alkyl groups.

$R^5$ is preferably $—(R^{31})_{p'}—(X^a)_{q'}—R^{32}—$. $R^{32}$ represents a single bond, $—(CH_2)_{t'}—$, or an o-, m- or p-phenylene group, and is preferably $—(CH_2)_{t'}—$. t' is an integer of 1 to 20, preferably an integer of 2 to 6, and more preferably an integer of 2 to 3. Here, $R^{32}$ (typically, hydrogen atoms in $R^{32}$) may be substituted with one or more substituents selected from $C_{1-3}$ alkyl groups.

Preferably, $R^5$ may be:
a single bond,
a $C_{1-20}$ alkylene group,

—R$^{31}$—X$^c$—R$^{32}$—, or
—X$^d$—R$^{32}$—
wherein R$^{31}$ and R$^{32}$ are as defined above. The alkylene group is a group having a —(C$_\delta$H$_{2\delta}$)— structure, may be substituted or unsubstituted, and may be linear or branched.

More preferably, R$^5$ is:
a single bond,
a C$_{2-20}$ alkylene group,
—(CH$_2$)$_s$X$^c$—,
—(CH$_2$)$_{s'}$—X$^c$—(CH$_2$)$_{t'}$—.
—X$^d$—, or
—X$^d$—(CH$_2$)$_{t'}$—, wherein
s' is an integer of 1 to 20, preferably an integer of 2 to 6, and more preferably an integer of 2 to 3, and
t' is as defined above.

In the above formula, X$^c$ represents:
—O—,
—S—,
—C(O)O—,
—CONR$^{34}$—,
—O—CONR$^{34}$—,
—Si(R$^{33}$)$_2$—.
—(Si(R$^{33}$)$_2$O)$_{m'}$—Si(R$^{33}$)$_2$—,
—O—(CH$_2$)$_{u'}$—(Si(R$^{33}$)$_2$O)$_{m'}$—Si(R$^{33}$)$_2$—,
—O—(CH$_2$)$_{u'}$—Si(R$^{33}$)$_2$—O—Si(R$^{33}$)$_2$—CH$_2$CH$_2$—Si(R$^{33}$)$_2$—O—Si(R$^{33}$)$_2$—,
—O—(CH$_2$)$_{u'}$—Si(OCH$_3$)$_2$O—Si(OCH$_3$)$_2$—,
—CONR$^{34}$—(CH$_2$)$_{u'}$—(Si(R$^{33}$)$_2$O)$_{m'}$—Si(R$^{33}$)$_2$—,
—CONR$^{34}$—(CH$_2$)$_{u'}$—N(R$^{34}$)—, or
—CONR$^{34}$-(o-, m- or p-phenylene)-Si(R$^{33}$)$_2$—, wherein
R$^{33}$, R$^{34}$, and m' are as fined above, and
u' is an integer of 1 to 20, preferably an integer of 2 to 6, and more preferably an integer of 2 to 3. X$^c$ is preferably —O—.

In the above formula, X$^d$ represents:
—S—,
—C(O)O—,
—CONR$^{34}$—,
—CONR$^{34}$—(CH$_2$)$_{u'}$—(Si(R$^{33}$)$_2$O)$_{m'}$—Si(R$^{33}$)$_2$—,
—CONR$^{34}$—(CH$_2$)$_{u'}$—N(R$^{34}$)—, or
—CONR$^{34}$-(o-, m- or p-phenylene)-Si(R$^{33}$)$_2$—, wherein
each symbol is as defined above.

More preferably, R$^5$ may be:
a single bond,
a C$_{2-20}$ alkylene group, —(CH$_2$)$_{s'}$—X$^c$—(CH$_2$)$_{t'}$—, or —X$^d$—(CH$_2$)$_{t'}$, wherein each symbol is as defined above.

Even more preferably, R$^5$ is:
a single bond,
a C$_{2-20}$ alkylene group,
—(CH$_2$)$_{s'}$—O—(CH$_2$)$_{t'}$—,
—(CH$_2$)$_{s'}$—(Si(R$^{33}$)$_2$O)$_{m'}$—Si(R$^{33}$)$_2$—(CH$_2$)$_{t'}$—,
—(CH$_2$)$_{s'}$—O—(CH$_2$)$_{u'}$—(Si(R$^{33}$)$_2$O)$_{m'}$—Si(R$^{33}$)$_2$—(CH$_2$)$_{t'}$—, or
—(CH$_2$)$_{s'}$—O—(CH$_2$)$_{t'}$—Si(R$^{33}$)$_2$—(CH$_2$)$_{u'}$—Si(R$^{33}$)$_2$—(C$_v$H$_{2v}$)—, wherein
R$^{33}$, m', s', t', and u' are as defined above, and v is an integer of 1 to 20, preferably an integer of 2 to 6, and more preferably an integer of 2 to 3.

In the above formula, —(C$_v$H$_{2v}$)— may be linear or branched, and may be, for example, —CH$_2$—, —CH$_2$CH$_2$—, CH$_2$CH$_2$CH$_2$—, —CH(CH$_3$)—, or —CH(CH$_3$)CH$_2$—.

R$^5$ may be substituted with one or more substituents selected from a fluorine atom, a C$_{1-3}$ alkyl group, and a C$_{1-3}$ fluoroalkyl group (preferably a C$_{1-3}$ perfluoroalkyl group).

In another embodiment, examples of R$^5$ include the following groups:

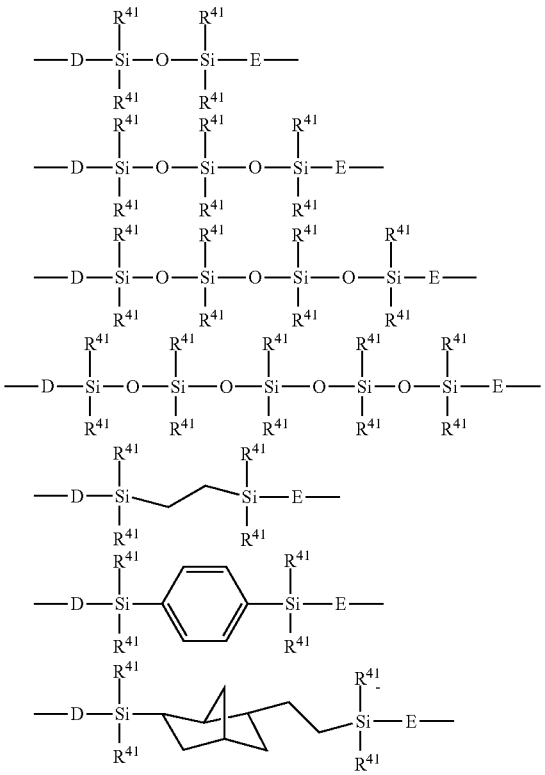

wherein
R$^{41}$ is each independently a hydrogen atom, a phenyl group, an alkyl group having 1 to 6 carbon atoms, or a C$_{1-6}$ alkoxy group, and is preferably a methyl group;
D is a group selected from
—CH$_2$O(CH$_2$)$_2$—,
—CH$_2$O(CH$_2$)$_3$—,
—CF$_2$O(CH$_2$)$_3$—,
—(CH$_2$)$_2$—,
—(CH$_2$)$_3$—,
—(CH$_2$)$_4$—,
—CONH—(CH$_2$)$_3$—,
—CON(CH$_3$)—(CH$_2$)$_3$—,
—CON(Ph)-(CH$_2$)$_3$— wherein Ph means phenyl, and

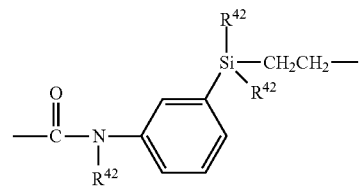

wherein R$^{42}$ each independently represents a hydrogen atom, a C$_{1-6}$ alkyl group or a C$_{1-6}$ alkoxy group, preferably a methyl group or a methoxy group, and more preferably a methyl group,
E is —(CH$_2$)$_{ne}$— wherein ne is an integer of 2 to 6, D is bonded to PFPE of the molecular backbone, and E is bonded to the group opposite to PFPE.

Specific examples of R$^5$ include:
a single bond
—CH$_2$OCH$_2$—,
—CH$_2$O(CH$_2$)$_2$—.

—CH$_2$O(CH$_2$)$_3$—.
—CH$_2$O(CH$_2$)$_6$—.
—CH$_2$O(CH$_2$)$_3$Si(CH$_3$)$_2$OSi(CH$_3$)$_2$(CH$_2$)$_2$—,
—CH$_2$O(CH$_2$)$_3$Si(CH$_3$)$_2$OSi(CH$_3$)$_2$OSi(CH$_3$)$_2$(CH$_2$)$_2$—,
—CH$_2$O(CH$_2$)$_3$Si(CH$_3$)$_2$O(Si(CH$_3$)$_2$O)$_2$Si(CH$_3$)$_2$(CH$_2$)$_2$—,
—CH$_2$O(CH$_2$)$_3$Si(CH$_3$)$_2$O(Si(CH$_3$)$_2$O)$_2$Si(CH$_3$)$_2$(CH$_2$)$_2$—,
—CH$_2$O(CH$_2$)$_3$Si(CH$_3$)$_2$O(Si(CH$_3$)$_2$O)$_{10}$Si(CH$_3$)$_2$(CH$_2$)$_2$—,
—CH$_2$O(CH$_2$)$_3$Si(CH$_3$)$_2$O(Si(CH$_3$)$_2$O)$_{20}$Si(CH$_3$)$_2$(CH$_2$)$_2$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$) CF$_2$OCF$_2$—,
—CH$_2$OCH$_2$CF$_2$CF$_2$OCF(CF$_3$) CF$_2$OCF$_2$CF$_2$—,
—CH$_2$OCH$_2$CF$_2$CF$_2$OCF(CF$_3$) CF$_2$OCF$_2$CF$_2$CF$_2$—,
—CH$_2$OCH$_2$CHFCF$_2$OCF$_2$—
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$) CF$_2$OCF$_2$—,
—CH$_2$OCH$_2$CHFCF$_2$OCF(CF$_3$) CF$_2$OCF$_2$CF$_2$—,
—CH$_2$OCH$_2$CHFCF$_2$OCF(CF$_3$) CF$_2$OCF$_2$CF$_2$CF$_2$—,
—CH$_2$OCF$_2$CHFOCF$_2$CF$_2$CF$_2$—C(O)NH—CH$_2$—,
—CH$_2$OCH$_2$(CH$_2$)$_7$CH$_2$Si(OCH$_3$)$_2$Si(OCH$_3$)$_2$(CH$_2$)$_2$OSi(OCH$_3$)$_2$OSi(OCH$_3$)$_2$(CH$_2$)$_2$—,
—CH$_2$OCH$_2$CH$_2$CH$_2$Si(OCH$_3$)$_2$OSi(OCH$_3$)$_2$(CH$_2$)$_3$—,
—CH$_2$OCH$_2$CH$_2$CH$_2$Si(OCH$_2$CH$_3$)$_2$OSi(OCH$_2$CH$_3$)$_2$(CH$_2$)$_3$—,
—CH$_2$OCH$_2$CH$_2$CH$_2$Si(OCH$_3$)$_2$OSi(OCH$_3$)$_2$(CH$_2$)$_2$—,
—CH$_2$OCH$_2$CH$_2$CH$_2$Si(OCH$_2$CH$_3$)$_2$OSi(OCH$_2$CH$_3$)$_2$(CH$_2$)$_2$—,
—(CH$_2$)$_2$—Si(CH$_3$)$_2$—(CH$_2$)$_2$—,
—(CH$_2$)$_2$—,
—(CH$_2$)$_3$—,
—(CH$_2$)$_4$—,
—(CH$_2$)$_5$—,
—(CH$_2$)$_6$—,
—CONH—CH$_2$—,
—CONH—(CH$_2$)$_2$—,
—CONH—(CH$_2$)$_3$—,
—CON(CH$_3$)—(CH$_2$)$_3$,
—CON(Ph)-(CH$_2$)$_3$— wherein Ph means phenyl, and
—CONH—(CH$_2$)$_6$—,
—CON(CH$_3$)—(CH$_2$)$_6$—,
—CON(Ph)-(CH$_2$)$_6$— wherein Ph means phenyl, and
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
—(CH$_2$)$_2$S(CH$_2$)$_3$—.
—CONH—(CH$_2$)$_3$Si(CH$_3$)$_2$OSi(CH$_3$)$_2$ (CH$_2$)$_2$—,
—CONH—(CH$_2$)$_3$Si(CH$_3$)$_2$OSi(CH$_3$)$_2$OSi(CH$_3$)$_2$(CH$_2$)$_2$—,
—CONH—(CH$_2$)$_3$Si(CH$_3$)$_2$O(Si(CH$_3$)$_2$O)$_2$Si(CH$_3$)$_2$(CH$_2$)$_2$—,
—CONH—(CH$_2$)$_3$Si(CH$_3$)$_2$O(Si(CH$_3$)$_2$O)$_3$Si(CH$_3$)$_2$(CH$_2$)$_2$—,
—CONH—(CH$_2$)$_3$Si(CH$_3$)$_2$O(Si(CH$_3$)$_2$O)$_{10}$Si(CH$_3$)$_2$(CH$_2$)$_2$—,
—CONH—(CH$_2$)$_3$Si(CH$_3$)$_2$O(Si(CH$_3$)$_2$O)$_{20}$Si(CH$_3$)$_2$(CH$_2$)$_2$—,
—C(O)O—(CH$_2$)$_3$—.
—C(O)O—(CH$_2$)$_6$—,
—CH$_2$—O—(CH$_2$)$_3$—Si(CH$_3$)$_2$—(CH$_2$)$_2$—Si(CH$_3$)$_2$—(CH$_2$)$_2$—,
—CH$_2$—O—(CH$_2$)$_3$Si(CH$_3$)$_2$(CH$_2$)$_2$—Si(CH$_3$)$_2$—CH(CH$_3$)—,
—CH$_2$—O—(CH$_2$)$_3$Si(CH$_3$)$_2$(CH$_2$)$_2$—Si(CH$_3$)$_2$—(CH$_2$)$_3$—,
—CH$_2$—O—(CH$_2$)$_3$Si(CH$_3$)$_2$(CH$_2$)$_2$Si(CH$_3$)$_2$—CH(CH$_3$)—CH$_2$—,
—O(CH$_2$)$_3$—,
—OCFHCF$_2$—,

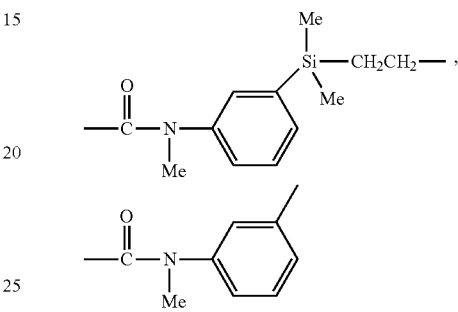

In one embodiment, R$^5$ is each independently at each occurrence a group represented by the following formula:

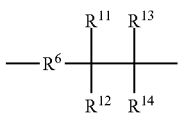

wherein
R$^6$ is a single bond or a divalent organic group;
R$_{11}$ is a hydrogen atom or an alkyl group having 1 to 6 carbon atoms;
R$^{12}$ is a hydrogen atom or an alkyl group having 1 to 6 carbon atoms;
R$^{13}$ is a hydrogen atom or an alkyl group having 1 to 6 carbon atoms; and
R$^{14}$ is a hydrogen atom or an alkyl group having 1 to 6 carbon atoms. Concerning this group, R$^6$ is bonded to Rf$^1$, and the other end is bonded to R$^4$.

In the above formula, R$^6$ is a single bond or a divalent organic group.

R$^6$ is preferably a single bond or a divalent hydrocarbon group.

R$^6$ is preferably a single bond or a group represented by the following formula:

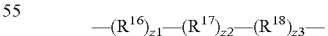

wherein
R$^{16}$ is each independently at each occurrence an alkylene group having 1 to 20 carbon atoms, preferably an alkylene group having 1 to 10 carbon atoms, more preferably an alkylene group having 1 to 6 carbon atoms, and even more preferably an alkylene group having 1 to 3 carbon atoms,
R$^{17}$ is each independently at each occurrence an arylene group having 6 to 20 carbon atoms, preferably an arylene group having 6 to 10 carbon atoms, and more preferably phenylene,
R$^{18}$ is an oxygen atom, z1 is an integer of 0 to 6, preferably an integer of 0 to 2, and more preferably 0 or 1, z2 is an integer of 0 to 6, preferably an integer of 0 to 2, and more preferably 0 or 1, z3 is an integer of 0 to 4, preferably an integer of 0 to 2, and more preferably 0 or 1, and the occurrence order of each repeating unit enclosed within parentheses provided with z1, z2, or z3 is arbitrary.

$R^6$ is preferably a group represented by:
a single bond,
—$R^{16}$—,
—$R^{17}$—,
—$R^{18}$—,
—$R^{16}$—$R^{17}$—,
—$R^{17}$—$R^{16}$—,
—$R^{16}$—$R^{16}$—,
—$R^{16}$—$R^{17}$—,
—$R^{16}$—$R^{18}$—,
—$R^{17}$—$R^{16}$—,
—$R^{16}$—$R^{16}$—$R^{16}$—,
—$R^{16}$—$R^{16}$—$R^{17}$—,
—$R^{17}$—$R^{16}$—$R^{16}$—, or
—$R^{17}$—$R^{16}$—$R^{17}$—, wherein $R^{16}$ is an alkylene group having 1 to 20 carbon atoms, preferably an alkylene group having 1 to 10 carbon atoms, more preferably an alkylene group having 1 to 6 carbon atoms, and even more preferably an alkylene group having 1 to 3 carbon atoms, $R^{17}$ is an arylene group having 6 to 20 carbon atoms, preferably an arylene group having 6 to 10 carbon atoms, and more preferably phenylene, and $R^{18}$ is an oxygen atom.

$R^6$ is more preferably a group represented by: a single bond,
—$R^{16}$—,
—$R^{16}$—$R^{18}$—, or
—$R^{16}$—$R^{18}$—$R^{16}$—, wherein $R^{16}$ is an alkylene group having 1 to 20 carbon atoms, preferably an alkylene group having 1 to 10 carbon atoms, more preferably an alkylene group having 1 to 6 carbon atoms, and even more preferably an alkylene group having 1 to 3 carbon atoms, and $R^{18}$ is an oxygen atom.

In one embodiment, $R^6$ is a single bond.
In one embodiment, $R^6$ is —$R^{16}$—.
In one embodiment, $R^6$ is —$R^{16}$—$R^{16}$—.

$R^{11}$, $R^{12}$, $R^{13}$, and $R^{14}$ are each independently preferably a hydrogen atom or an alkyl group having 1 to 3 carbon atoms, more preferably a hydrogen atom or a methyl group, and even more preferably a hydrogen atom.

In a preferable embodiment, $R^6$ is a single bond, —$R^{16}$—, or —$R^{16}$—$R^{16}$—, and $R^{11}$, $R^{12}$, $R^{13}$, and $R^{14}$ are hydrogen atoms.

In formula (1), s is 1 or 2. In one embodiment, s is 1. In another embodiment, s is 2.

In a preferable embodiment, $Rf^1$ is a fluoroalkyl group, a fluoroalkylene group, or a monovalent or divalent fluoropolyether group, and preferably a monovalent or divalent fluoropolyether group;

$R^2$ and $R^3$ are each independently at each occurrence a branched alkyl group having 3 to 6 carbon atoms or an aryl group having 6 to 10 carbon atoms, and preferably a tert-butyl group or a phenyl group;

$R^4$ is each independently at each occurrence —O— or —S—, and preferably —O—;

$R^5$ is each independently at each occurrence a group represented by the following formula:

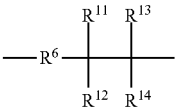

wherein $R^6$ is a single bond or a divalent organic group, and preferably a single bond, an alkylene group having 1 to 10 carbon atoms, or —$C_{1-10}$ alkylene-O—;

$R^{11}$ is a hydrogen atom or an alkyl group having 1 to 6 carbon atoms, and preferably a hydrogen atom;

$R^{12}$ is a hydrogen atom or an alkyl group having 1 to 6 carbon atoms, and preferably a hydrogen atom;

$R^{13}$ is a hydrogen atom or an alkyl group having 1 to 6 carbon atoms, and preferably a hydrogen atom; and $R^{14}$ is a hydrogen atom or an alkyl group having 1 to 6 carbon atoms, and preferably a hydrogen atom; and s is 1 or 2.

Next, a method for producing the compound of the present disclosure will now be described.

The compound represented by the above formula (1) can be produced by a method including the following steps:

(a) reacting a compound represented by formula (IV):

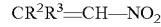

$CR^2R^3$=CH—$NO_2$ wherein $R^2$ and $R^3$ each represent a hydrogen atom or a hydrocarbon group with a compound represented by formula (V):

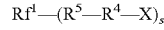

$Rf^1$—$(R^5$—$R^4$—$X)_s$ wherein $Rf^1$ is a fluoroalkyl group, a fluoroalkylene group, or a monovalent or divalent fluoropolyether group;

$R^4$ is each independently at each occurrence —O—, —S—, —$NR^7$—, or —O—P(=O)$OR^8$—;

$R^5$ is each independently at each occurrence a divalent hydrocarbon group having two or more carbon atoms in the main chain;

$R^7$ is each independently at each occurrence a hydrogen atom or a hydrocarbon group;

$R^8$ is each independently at each occurrence a hydrocarbon group;

s is 1 or 2;

X is each independently a hydrogen atom, Li, Na, K, Cs, Cu, —$MgX^a$, —$B(OR^{25})_3$, —$ZnX^a$, —$SiR^{26}_3$, —$Si(OR^{25})_3$, or a copper complex;

$X^a$ is a halogen atom;

$R^{25}$ is a hydrogen atom or a linear or branched alkyl (preferably methyl); and $R^{26}$ is alkyl or aryl, and preferably linear alkyl or phenyl, to obtain a compound of the following formula (II):

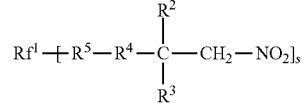

wherein each symbol is as defined with respect to formula (I); then (b) performing a dehydration treatment; and optionally (c) converting $R^2$ and $R^3$ to different $R^2$ and $R^3$.

In a preferable embodiment, X may be a hydrogen atom.

First, step (a) will now be described.

The compound represented by formula (IV) is commercially available or can be produced by a method known per-se.

The compound represented by formula (V) is a hetero atom-based nucleophile, and is commercially available or can be produced by a method known per-se.

The molar ratio of the compound represented by formula (IV) to the compound represented by formula (V) is not limited, and can be suitably selected according to the value of s in formula (I). For example, when s is 2, the molar ratio of the compound represented by formula (IV) to the compound represented by formula (V) is preferably 1:0.6 to 1:5, and particularly preferably 1:0.8 to 1:3.

The reaction is usually carried out in a solvent. The solvent is not limited as long as it is a solvent that does not deactivate the nucleophile represented by formula (V), and examples include cyclic ethers such as THF (tetrahydrofuran), tetrahydropyran, and dioxane, acyclic ethers such as diethyl ether, diisopropyl ether, dibutyl ether, monoglyme, diglyme, and triglyme, aromatic compounds such as HMPA (hexamethylphosphamide), DMPU (dimethylpropylene), TMEDA (tetramethylethylenediamine), toluene, xylene, and benzotrifluoride, amides such as N,N-dimethylformamide, N,N-dimethylacetamide, and N-methylpyrrolidone, and mixtures thereof.

The reaction temperature is suitably selected according to the nucleophile represented by formula (V) used and is, for example, a temperature at which the nucleophile used is not deactivated. Such a temperature can be easily determined by those skilled in the art.

The reaction time is usually 10 minutes to 24 hours such as 30 minutes to 3 hours.

The reaction is preferably carried out in the presence of a basic reagent. The basic reagent is not limited, and examples include inorganic bases such as NaH, CaH$_2$, LiH, LiAlH$_4$, NaBH$_4$, Cs$^t$OBu, K$^t$OBu, Na$^t$OBu, Li$^t$OBu, CsOH, KOH, NaOH, LiOH, Cs$_2$CO$_3$, K$_2$CO$_3$, Na$_2$CO$_3$, Li$_2$CO$_3$, CsHCO$_3$, KHCO$_3$, NaHCO$_3$, LiHCO$_3$, CsF, and tetra-n-butylammonium fluoride (TBAF), organic bases such as triethylamine, pyridine, N,N-dimethyl-4-aminopyridine (DMAP), diazabicycloundecene (DBU), and 1,4-diazabicyclo[2.2.2]octane (DABCO), and organolithium reagents such as $^n$BuLi, $^t$BuLi, and lithium diisopropylamide (LDA).

Next, step (b) will now be described.

Due to the dehydration treatment of step (b), the —CH$_2$NO$_2$ moiety of the compound represented by formula (II) is converted to —CNO, and thus a nitrile oxide compound can be obtained.

The dehydration treatment is not limited, and can be carried out with concentrated sulfuric acid, trifluoromethanesulfonic acid, trifluoromethanesulfonimide, phenyl isocyanate, or other strong acids having a non-nucleophilic counter anion.

In a preferable embodiment, the dehydration treatment is carried out with an isocyanate compound in the presence of a base, and particularly preferably with phenyl isocyanate in the presence of triethylamine.

The treatment temperature is usually −20° C. to 100° C. and preferably 0° C. to 50° C.

The treatment time is usually 1 minute to 300 minutes such as 10 to 60 minutes.

As is clear from above, the compound represented by formula (II) is an intermediate of the compound represented by formula (I).

Accordingly, the present disclosure provides a compound represented by formula (II):

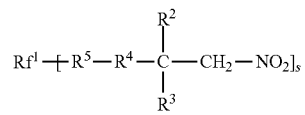

wherein

Rf$^1$ is a fluoroalkyl group, a fluoroalkylene group, or a monovalent or divalent fluoropolyether group;

R$^2$ and R$^3$ each independently at each occurrence represent a hydrogen atom or a hydrocarbon group;

R$^4$ is each independently at each occurrence —O—, —S—, —NR$^7$—, or —O—P(=O)OR$^8$—;

R$^5$ is each independently at each occurrence a divalent hydrocarbon group having two or more carbon atoms in the main chain;

R$^7$ is each independently at each occurrence a hydrogen atom or a hydrocarbon group;

R$^8$ is each independently at each occurrence a hydrocarbon group; and s is 1 or 2. In the formula, the details of each symbol are the same as those described in relation to formula (I).

Next, step (c) will now be described.

Step (c) is an optional step that converts R$^2$, R$^3$, and R$^4$ groups in the resulting nitrile oxide compound to other groups, and can be carried out by, for example, a method involving replacing such a group with another group or introducing a further substituent. A person skilled in the art can suitably carry out the step by a method known in the art.

The above reactions may be continuously carried out in one-pot, or isolation and purification may be carried out for each step.

In a preferable embodiment, it is preferable that after step (a), the resulting compound represented by formula (II) is isolated and purified, and then the dehydration treatment of step (b) is carried out with an isocyanate compound, preferably phenyl isocyanate, in the presence of a base, preferably triethylamine.

In another embodiment, it is possible that after step (a), the base in the system is deactivated with an acid, and the dehydration treatment of step (b) is directly carried out without isolation and purification.

In another embodiment, it is possible that after step (a), the base in the system is deactivated with an acid, washed with water or a suitable organic solvent, and subjected to a purification operation such as reprecipitation, and the dehydration treatment of step (b) is carried out with the resulting crude product.

As the above acid, hydrochloric acid, acetic acid, nitric acid, or sulfuric acid is usable, and hydrochloric acid or acetic acid is preferable.

Next, the composition of the present disclosure will now be described.

The present disclosure provides a composition (hereinafter also referred to as a composition of the present disclosure) containing one or more compounds (I) of the present disclosure described above. The composition may be liquid or solid. Moreover, the composition may be solely composed of the compound (I) of the present disclosure described above.

In one embodiment, the composition of the present disclosure may further contain, in addition to the compound (I) of the present disclosure, a material containing a group having reactivity with a nitrile oxide group. That is to say, in this embodiment, the composition of the present disclosure may be a mixture of the compound (I) of the present disclosure and a material containing a group having reactivity with a nitrile oxide group.

In another embodiment, the composition of the present disclosure may be in the form of a combination with another composition such as a composition containing a material containing a group having reactivity with a nitrile oxide group. In this embodiment, the composition of the present disclosure and another composition can be mixed immediately before use and used in the desired application.

In the combination form, both the composition of the present disclosure and another composition may be liquid, one may be solid (including gel), or both may be solid (including gel).

The composition of the present disclosure may contain a solvent. The solvent can be suitably selected according to the components contained in the composition.

In a preferable embodiment, the composition of the present disclosure or the combination form of the composition of the present disclosure and another composition is used to be applied to a material containing a group having reactivity with a nitrile oxide group.

Examples of the "group having reactivity with a nitrile oxide group" include groups having a double bond (C=C, C=N, N=N, C=S, P(V)=C, C=P(III), C=As, C=Se, B=N, P(V)=N, C=O) and groups having a triple bond (C≡C, C≡N, C≡P), and specific examples include an alkenyl group, an alkynyl group, and a nitrile group.

The "material" of the material containing a group having reactivity with a nitrile oxide group are not limited, and examples include any organic materials (such as resins, polymeric compounds, and other compounds) and inorganic materials (such as glass, ceramics, and metals).

In one embodiment, the composition of the present disclosure is a surface-treating agent.

The surface-treating agent of the present disclosure contains at least one compound (I) of the present disclosure described above as a main component or active component, is capable of forming a surface-treating layer having water-repellency, oil-repellency, antifouling properties, friction durability, surface lubricity, waterproof properties, and the like, and is suitably used as an antifouling coating agent or a water-proof coating agent. Here, the "main component" refers to a component most abundantly contained in the surface-treating agent, such as a component the content of which in the surface-treating agent exceeds 50%, and the "active component" means a component that remains on the base material to be treated, forms a surface-treating layer, and can exert a certain function (such as water-repellency, oil-repellency, antifouling properties, surface lubricity, and friction durability).

The surface-treating agent of the present disclosure is more advantageous by being suitably applicable to any base material as long as the base material has reactivity with a nitrile oxide group than a surface-treating agent containing a fluorine-containing silane compound suitably used mainly on a glass base material and a surface-treating agent containing a compound having a curable site (such as a double bond) suitably used mainly on a resin base material.

The composition of the surface-treating agent of the present disclosure may be suitably selected according to the desired function of the surface-treating layer.

For example, the surface-treating agent may contain, in addition to the compound (I) of the present disclosure described above, a fluoropolyether compound, preferably a perfluoropolyether compound, that can be understood as a fluorine-containing oil (hereinafter also referred to as a "fluorine-containing oil"). The fluorine-containing oil contributes to increasing the surface lubricity of the surface-treating layer.

In the surface-treating agent, the fluorine-containing oil may be contained in an amount of, for example, 0 to 300 parts by mass and preferably 50 to 200 parts by mass based on 100 parts by mass of the compound (I) of the present disclosure (the total amount of two or more when present; the same applies below).

When the compound (I) of the present disclosure contains a perfluoroalkyl group, the fluorine-containing oil may be a compound represented by general formula $Rf^1$—F wherein $Rf^1$ is a perfluoroalkyl group as contained in the compound (I) of the present disclosure. In this case, the compound represented by $Rf^1$—F is preferable in that an increased affinity with the compound (I) of the present disclosure is obtained.

The surface-treating agent of the present disclosure may contain, in addition to the compound (I) of the present disclosure, a silicone compound that can be understood as a silicone oil (hereinafter referred to as a "silicone oil").

The silicone oil contributes to increasing the surface lubricity of the surface-treating layer.

In the surface-treating agent, the silicone oil may be contained in an amount of, for example, 0 to 300 parts by mass and preferably 50 to 200 parts by mass based on 100 parts by mass of the compound (I) of the present disclosure.

For example, a linear or cyclic silicone oil having 2000 or less siloxane bonds can be used as such a silicone oil. The linear silicone oil may be a so-called straight silicone oil or modified silicone oil. Examples of the straight silicone oil include dimethyl silicone oil, methylphenyl silicone oil, and methylhydrogen silicone oil. Examples of the modified silicone oil include those obtained by modifying the straight silicone oil with alkyl, aralkyl, polyether, higher fatty acid ester, fluoroalkyl, amino, epoxy, carboxyl, alcohol, or the like. Examples of the cyclic silicone oil include a cyclic dimethyl siloxane oil.

The present disclosure also provides an article containing a base material and a layer (a surface-treating layer) formed of the compound (I) of the present disclosure described above or a surface-treating agent (hereinafter these are simply referred to as a surface-treating agent collectively) on the surface of the base material. Such an article can be produced, for example, as follows.

First, the base material is provided. As described above, the surface-treating agents of the present disclosure can be suitably applied to any base material that has reactivity with a nitrile oxide group. Such a base material may be composed of any suitable material such as glass, resin (natural or synthetic resin, which may be a commonly used plastic material and may be in a plate, film, or another form), metal (which may be a simple metal such as aluminum, copper or iron, or a composite such as alloy), ceramics, semi-conductors (such as silicon and germanium), fiber (such as a woven fabric and a nonwoven fabric), fur, leather, wood, potteries, and stone materials.

For example, when the article to be produced is an optical member, the material that constitutes the surface of the base material may be a material for an optical member, such as glass or a transparent plastic. Also, when the article to be produced is an optical member, some layer (or film) such as a hard coat layer or an antireflection layer may be formed on the surface (the outermost layer) of the base material. Any of a single-layer antireflection layer and a multilayer antireflection layer may be used for the antireflection layer. Examples of inorganic materials usable in the antireflection layer include $SiO_2$, SiO, $ZrO_2$, $TiO_2$, TiO, $Ti_2O_3$, $Ti_2O_5$, $Al_2O_3$, $Ta_2O_5$, $CeO_2$, MgO, $Y_2O_3$, $SaO_2$, $MgF_2$, and $WO_3$. These inorganic substances may be used singly or in combinations (for example, as a mixture) of two or more thereof. According to its specific specification or the like, the base material may have an insulating layer, an adhesive layer, a protecting layer, a decorated frame layer (I—CON), an atomizing layer, a hard coating layer, a polarizing film, a phase difference film, a liquid crystal display module, or the like.

The shape of the base material is not limited. Also, the surface region of the base material, on which the surface-treating layer is to be formed, may be at least a part of the surface of the base material, and can be suitably determined according to the application, the specific specification, and the like of the article to be produced.

As for the base material, while at least the surface portion thereof may be composed of a material that originally has a group having reactivity with a nitrile oxide group, a group having reactivity with a nitrile oxide group may be introduced into the base material by pretreatment. For example, a glass base material is treated with a piranha solution to cause a hydroxyl group to appear on the surface of the base material, and this hydroxyl group is reacted with, for example, allyltrichlorosilane, thereby enabling an allyl group, which is a group having reactivity with a nitrile oxide group, to be introduced to the surface of the base material.

Next, a film of the surface-treating agent described above is formed on the surface of the base material, this film is post-treated as necessary, and, thereby, a surface-treating layer is formed from the surface-treating agent.

The formation of a film of the surface-treating agent of the present disclosure can be carried out by applying the surface-treating agent to the surface of the base material so as to coat the surface. The coating method is not limited. For example, a wet coating method is usable.

Examples of the wet coating method include dip coating, spin coating, flow coating, spray coating, roll coating, gravure coating, microgravure coating, bar coating, die coating, and similar methods.

Examples of the dry coating method include vacuum deposition, sputtering, CVD, and similar methods. Specific examples of the vacuum deposition method include resistance heating, electron beam, high-frequency heating, ion beam, and similar methods. Specific examples of the CVD method include plasma-CVD, optical CVD, thermal CVD, and similar methods.

Moreover, coating by an atmospheric pressure plasma method is also possible.

When using the wet coating method, the surface-treating agent of the present disclosure may be diluted with a solvent and then applied to the surface of the base material. From the viewpoint of the stability of the fluorine-containing silane compound or the composition and the volatility of the solvent, the following solvents are preferably used: perfluoroaliphatic hydrocarbons having 5 to 12 carbon atoms (for example, perfluorohexane, perfluoromethylcyclohexane, and perfluoro-1,3-dimethylcyclohexane); polyfluoroaromatic hydrocarbons (for example, bis(trifluoromethyl)benzene); polyfluoroaliphatic hydrocarbons; alkyl perfluoroalkyl ethers (the perfluoroalkyl group and the alkyl group may be linear or branched) such as hydrofluoroether (HFE) (for example, perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF(OCH_3)C_3F_7$)). These solvents can be used singly or as a mixture of two or more. In particular, hydrofluoroether is preferable, and perfluorobutyl methyl ether ($C_4F_9OCH_3$) and/or perfluorobutylethyl ether ($C_4F_9OC_2H_5$) is particularly preferable.

After forming a film of the surface-treating agent by the above method, post-treatment may be carried out as necessary. The post-treatment is not limited, and an example may be heating to 40 to 150° C., such as 60 to 100° C.

In the above-described manner, a surface-treating layer derived from the surface-treating agent of the present disclosure is formed on the surface of the base material, and thus an article is produced.

Accordingly, the surface-treating agent of the present disclosure can be suitably used to form a surface-treating layer on the outermost layer of an optical material. The optical material preferably includes a wide variety of optical materials: for example, displays such as cathode ray tubes (CRTs; for example, TV, PC monitors), liquid crystal displays, plasma displays, organic EL displays, inorganic thin-film EL dot matrix displays, rear projection displays, vacuum fluorescent displays (VFDs), field emission displays (FEDs); protective plates for such displays; and those obtained by performing an antireflection film treatment on their surfaces.

The article having a surface-treating layer obtained according to the present disclosure may be, but is not limited to, an optical member. Examples of the optical member include lenses of glasses or the like; front surface protective plates, antireflection plates, polarizing plates, and anti-glare plates for displays such as PDPs, LCDs; touch panel sheets for devices such as mobile phones and personal digital assistants; disc surfaces of optical discs such as Blu-ray® discs, DVD discs, CD-Rs, and MOs; and optical fibers.

The thickness of the surface-treating layer is not limited. In the case of an optical member, the thickness of the surface-treating layer is preferably in the range of 0.1 to 30 μm and preferably 0.5 to 20 μm in terms of optical performance, surface lubricity, friction durability, and antifouling property.

The surface-treating layer obtained from the surface-treating agent of the present disclosure has, for example, water-repellency, oil-repellency, antifouling properties, surface lubricity, waterproof properties, and/or friction durability, and may be suitably utilized as a functional thin film.

In one embodiment, the composition of the present disclosure is a modification treatment agent.

The modification treatment agent of the present disclosure contains at least one compound (I) of the present disclosure described above, and can alter the solubility of a base material such as a polymer material in an organic solvent.

While the modification treatment agent of the present disclosure can exhibit its function solely with the compound (I) of the present disclosure described above, it may further contain a solvent.

The solvent is not limited as long as it can dissolve the compound (I) of the present disclosure or is compatible with the compound (I) of the present disclosure, and examples include fluorine-containing aliphatic or aromatic hydrocarbons, specifically perfluorohexane and bis(trifluoromethyl)benzene.

The modification treatment agent of the present disclosure can also be suitably used with any base material (for example, a polymer material) as long as it has reactivity with a nitrile oxide group.

Such a polymer material is not limited, and examples include PAN (polyacrylonitrile) having a nitrile group (C≡N) within the molecule, NR (natural rubber) having a carbon-carbon double bond (C=C) within the molecule, EPDM (ethylene-propylene-diene copolymer rubber), polynorbornene, and NBR (nitrile rubber) having a nitrile group and a carbon-carbon double bond within the molecule.

The modification treatment involving the modification treatment agent of the present disclosure is not limited, and can be carried out by bringing the compound (I) of the present disclosure into contact with a polymer material in an organic solvent or without a solvent.

The organic solvent is not limited, and is preferably a solvent in which both the polymer material and the compound (I) of the present disclosure readily dissolve.

Specific examples include chloroform and DMF (N,N-dimethylformamide).

When carried out without a solvent, the modification treatment may be carried out in air or may be carried out in an atmosphere filled with inert gas.

The inert gas is not limited, and examples include argon and nitrogen.

When carrying out the modification treatment without a solvent, the modification treatment is preferably carried out with a kneading apparatus.

The kneading apparatus is not limited, and examples include kneaders such as a biaxial kneader, a closed kneader, a Banbury mixer, and an intermix, and extruders such as a biaxial extruder, a monoaxial extruder, and a multi-axial extruder.

The temperature of the modification treatment is not limited as long as it is a temperature at which the compound (I) of the present disclosure reacts with the polymer material, and, for example, since it is a chemical reaction, a higher temperature results in a more accelerated reaction, and the management of the production process is easier when the temperature adjustment such as heating is not performed, and therefore the temperature is preferably 0 to 150° C. Furthermore, when the polymer material has at least a carbon-carbon double bond as a multiple bond as in NBR, NR, EPDM, or the like, the temperature is more preferably 20 to 100° C., and when the polymer material has only a triple bond as a multiple bond as in PAN or the like, the temperature is more preferably 60 to 150° C.

The present disclosure also provides a modified material such as a modified polymer material treated with the above modification treatment agent.

The modified polymer material modified with the modification treatment agent of the present disclosure has an altered solubility in various organic solvents, and has an improved resistance to sunlight and ozone and thus an increased durability.

In one embodiment, the composition of the present disclosure is a filler modifier.

The filler modifier of the present disclosure contains at least one compound (I) of the present disclosure described above.

The filler to which the filler modifier of the present disclosure is applied is a filler, the surface of which has a group having reactivity with a nitrile oxide group, and examples include, but are not limited to, silica particles, alumina, titanium oxide, barium oxide, and calcium oxide, to the surface of which a group having an unsaturated bond such as a vinyl group, an allyl group, or a nitrile group is introduced.

A method for introducing a group having an unsaturated bond such as a vinyl group, an allyl group, or a nitrile group to the surface of silica particles is well known to those skilled in the art. For example, introduction of a vinyl group to the surface of silica particles can be carried out by treating the silica particles with a vinyl-based silane coupling agent (for example, vinylethoxysilane).

The modification treatment involving the filler modifier of the present disclosure can be carried out simply by mixing the filler modifier with a filler. Such a modification treatment is preferably carried out in a solvent.

The solvent is not limited as long as it is inert to the compound of the present disclosure and the filler, and examples include water, perfluoroaliphatic hydrocarbons having 5 to 12 carbon atoms (for example, perfluorohexane, perfluoromethylcyclohexane, and perfluoro-1,3-dimethylcyclohexane); polyfluoroaromatic hydrocarbons (for example, bis(trifluoromethyl)benzene); polyfluoroaliphatic hydrocarbons; and alkyl perfluoroalkyl ethers (the perfluoroalkyl group and the alkyl group may be linear or branched) such as hydrofluoroether (HFE) (for example, perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF(OCH_3)C_3F_7$)).

Moreover, the present disclosure provides a filler, such as silica particles, treated with the filler modifier.

The filler treated with the filler modifier of the present disclosure, for example, when used as a filler for fluoroelastomer, perfluoroelastomer, and fluororesin provides the effect of improving dispersibility or enabling a reaction between the reactive group of the filler surface (for example, $SiO_2$ of silica) and a fluorine-containing polymer to be suppressed, as compared with an untreated filler.

In one embodiment, the composition of the present disclosure is a reactive compatibilizer.

The reactive compatibilizer of the present disclosure contains at least one compound represented by formula (I) of the present disclosure described above, and is capable of increasing miscibility between two or more materials (compounds). For example, the reactive compatibilizer of the present disclosure can increase miscibility between a general-purpose polymer (a fluorine-free polymer) having reactivity with a nitrile oxide group and a fluorine-containing polymer.

The compound having reactivity with a nitrile oxide group is not limited as long as it is the above-described polymer having a moiety that has reactivity with a nitrile oxide group (preferably C=C, C≡N) within the molecule. The moiety that has reactivity with a nitrile oxide group may be present in the skeleton itself of a polymer that will be described below, and when not present, a substituent having a moiety that has reactivity with a nitrile oxide group may be introduced.

Examples of the general-purpose polymer include polymers containing an aromatic ring in the main chain or a side chain (such as polystyrene, polyamide, polyimide, polycarbonate, polyphenylene ether, polyalkylene terephthalate, polysulfone, polyphenylene sulfide, and polyaryl ether ketone), polypropylene, polyethylene, etc., or natural rubber, NBR (nitrile rubber), EPDM (ethylene-propylene-diene copolymer rubber), PAN (polyacrylonitrile), polynorbornene, $H_2C=C(R)-(CH_2-CHR)_n-CH_2-CR=CH_2$ (wherein R is each independently a hydrogen atom, a methyl group, an ethyl group, or an isobutyl group, and n is an integer of 10 to 1000).

The fluorine-containing compound is not limited, and examples include fluororesin and fluoroelastomer.

Examples of the fluororesin include non melt-processible fluororesin such as polytetrafluoroethylene (PTFE), and melt-fabricable fluororesin.

PTFE may be a homopolymer of tetrafluoroethylene (TFE) or modified polytetrafluoroethylene (modified PTFE).

Herein, "modified PTFE" means what is obtained by copolymerizing TFE with such a small amount of a comonomer that the comonomer does not impart melt-fabricability to the resulting copolymer. The small amount of a comonomer is not limited, and examples include hexafluoropropylene (HFP), chlorotrifluoroethylene (CTFE), trifluoroethylene (TrFE), perfluoro(alkyl vinyl ether) (PAVE), perfluoro (alkoxyalkyl vinyl ether), and (perfluoroalkyl)ethylene. As for the small amount of a comonomer, one or two or more of such monomers can be used.

Examples of PAVE include perfluoro(methyl vinyl ether), perfluoro(ethyl vinyl ether), and perfluoro(propyl vinyl ether).

The proportion of the small amount of a comonomer added to the modified PTFE varies depending on its kind, and, for example, when PAVE, perfluoro(alkoxyalkyl vinyl ether), or the like is used, usually the proportion is preferably 0.001 to 1% by mass of the total mass of TFE and the small amount of a comonomer.

Examples of the melt-fabricable fluororesin include a tetrafluoroethylene (TFE)/hexafluoropropylene (HFP) copolymer, a TFE/HFP/perfluoro(alkyl vinyl ether) (PAVE) copolymer, a TFE/PAVE copolymer (a tetrafluoroethylene-perfluoroalkyl vinyl ether copolymer (PFA) and a tetrafluoroethylene-perfluoromethyl vinyl ether copolymer (MFA)), an ethylene (Et)/TFE copolymer, an Et/TFE/HFP copolymer, a polychlorotrifluoroethylene (PCTFE), a chlorotrifluoroethylene (CTFE)/TFE copolymer, an Et/CTFE copolymer, a TFE/vinylidene fluoride (VDF) copolymer, a VDF/HFP/TFE copolymer, and a VDF/HFP copolymer.

Further examples of the fluororesin include hydroxyl group-containing fluorine-containing copolymers that contain a fluoroolefin unit and a hydroxyl group-containing radically polymerizable unsaturated monomer unit.

Examples of the fluoroolefin unit include one or two or more of a tetrafluoroethylene (TFE) unit, a chlorotrifluoroethylene (CTFE) unit, a vinyl fluoride (VF) unit, a vinylidene fluoride (VDF) unit, a hexafluoropropylene (HFP) unit, a trifluoroethylene (TrFE) unit, and a perfluoro (alkyl vinyl ether) (PAVE) unit, and examples of the PAVE unit include a perfluoromethyl vinyl ether unit and a perfluoropropyl vinyl ether unit.

Examples of the combination of two or more units containing a TFE unit include a TFE/HFP unit, a TFE/PAVE unit, a TFE/ethylene unit, a TFE/vinyl ether unit, a TFE/vinyl ester unit, a TFE/vinyl ester/vinyl ether unit, and a TFE/vinyl ether/allyl ether unit. Among these, from the viewpoint of being favorably mixed with an ethylenically unsaturated group-containing monomer, a TFE/ethylene unit, a TFE/vinyl ether unit, a TFE/vinyl ester unit, a TFE/vinyl ester/vinyl ether unit, a TFE/vinyl ether/allyl ether unit, and the like are preferable.

Examples of the combination of two or more units containing a CTFE unit include a CTFE/HFP unit, a CTFE/PAVE unit, a CTFE/ethylene unit, a CTFE/vinyl ether unit, a CTFE/vinyl ester unit, a CTFE/vinyl ester/vinyl ether unit, and a CTFE/vinyl ether/allyl ether unit. Among these, from the viewpoint of being favorably mixed with an ethylenically unsaturated group-containing monomer, a CTFE/ethylene unit, a CTFE/vinyl ether unit, a CTFE/vinyl ester unit, a CTFE/vinyl ester/vinyl ether unit, a CTFE/vinyl ether/allyl ether unit, and the like are preferable.

Likewise, examples of the combination of two or more units containing a HFE unit include a CTFE/HFP unit, a TFE/HFP unit, a HFP/vinyl ether unit, a HFP/vinyl ester unit, a HFP/vinyl ester/vinyl ether unit, and a HFP/vinyl ether/allyl ether unit. Among these, from the viewpoint of being favorably mixed with an ethylenically unsaturated group-containing monomer, a HFP/vinyl ether unit, a HFP/vinyl ester unit, a HFP/vinyl ester/vinyl ether unit, a HFP/vinyl ether/allyl ether unit, and the like are preferable.

Examples of the combination of two or more units containing a VDF unit include a VDF/TFE unit, a VDF/HFP unit, a VDF/TFE/HFP unit, a VDF/CTFE unit, a VDF/TFE/PAVE unit, a VDF/CTFE/TFE unit, and a VDF/CTFE/HFP unit. Among these, from the viewpoint of being favorably mixed with an ethylenically unsaturated group-containing monomer, the VDF unit is preferably contained in a polymer in an amount of 50 mol % or more.

Specific examples of the hydroxyl group-containing radically polymerizable unsaturated monomer unit in the hydroxyl group-containing fluorine-containing copolymer include hydroxyalkyl vinyl ether and hydroxyalkyl allyl ether represented by the following formula:

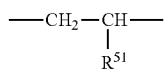

wherein $R^{51}$ is $-OR^{52}$ or $-CH_2OR^{52}$, provided that $R^{52}$ is an alkyl group having a hydroxyl group. In $R^{52}$, for example, to 3 and preferably 1 hydroxyl group is bonded to a linear or branched alkyl group having 1 to 8 carbon atoms. Examples thereof include a 2-hydroxyethyl vinyl ether unit, a 3-hydroxypropyl vinyl ether unit, a 2-hydroxypropyl vinyl ether unit, a 2-hydroxy-2-methylpropyl vinyl ether unit, a 4-hydroxybutyl vinyl ether unit, a 4-hydroxy-2-methylbutyl vinyl ether unit, a 5-hydroxypentyl vinyl ether unit, a 6-hydroxyhexyl vinyl ether unit, a 2-hydroxyethyl allyl ether unit, a 4-hydroxybutyl allyl ether unit, an ethylene glycol monoallyl ether unit, a diethylene glycol monoallyl ether unit, a triethylene glycol monoallyl ether unit, and a glycerin monoallyl ether unit, and among these, especially hydroxyalkyl vinyl ethers having 3 to 8 carbon atoms and, in particular, a 4-hydroxybutyl vinyl ether unit and a 2-hydroxyethyl vinyl ether unit are preferable from the viewpoint of the ease of polymerization.

The hydroxyl group-containing fluorine-containing copolymer may further contain a fluorine-free vinyl ether unit and/or a fluorine-free vinyl ester unit that does not contain a hydroxyl group.

Specific examples of the fluorine-free vinyl ether unit and/or the fluorine-free vinyl ester unit that does not contain a hydroxyl group in the hydroxyl group-containing fluorine-containing copolymer include alkyl vinyl ether and alkyl allyl ether represented by the following formula:

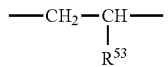

wherein $R^{53}$ is $-OR^{54}$, $-COOR^{54}$, or $-OCOR^{54}$, provided that $R^{54}$ is an alkyl group. $R^{54}$ is, for example, a linear, branched, or cyclic alkyl group having 1 to 8 carbon atoms. Preferable examples thereof include a cyclohexyl vinyl ether unit, a methyl vinyl ether unit, an ethyl vinyl ether unit, a propyl vinyl ether unit, a n-butyl vinyl ether unit, an isobutyl vinyl ether unit, a vinyl acetate unit, a vinyl propionate unit, a vinyl butyrate unit, a vinyl isobutyrate unit, a vinyl pivalate unit, a vinyl caproate unit, a vinyl versatate unit, a vinyl laurate unit, a vinyl stearate unit, and a vinyl cyclohexylcarboxylate unit. Moreover, examples in terms of superior weather resistance, solubility, and cost include vinyl versatate, vinyl laurate, vinyl stearate, vinyl cyclohexylcarboxylate, and vinyl acetate. Among these, in terms of chemical resistance, preferable are a non-aromatic carboxylic acid vinyl ester, in particular a carboxylic acid vinyl ester having 6 or more carbon atoms, and more preferably a carboxylic acid vinyl ester having 9 or more carbon atoms. The upper limit of the number of carbon atoms of the carboxylic acid in the carboxylic acid vinyl ester is preferably 20 or less and more preferably 15 or less. As a specific example, vinyl versatate is most preferable.

The hydroxyl group-containing fluorine-containing copolymer may contain a carboxyl group-containing monomer unit.

The carboxyl group-containing monomer unit contains a carboxyl group and does not contain a hydroxyl group and an aromatic group, and is different from other units in this respect.

Examples of the carboxyl group-containing monomer unit include carboxyl group-containing vinyl monomers represented by the following formulas:

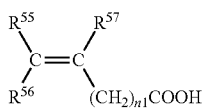

wherein $R^{55}$, $R^{56}$, and $R^{57}$ are the same or different, and are each independently a hydrogen atom, an alkyl group, a carboxyl group, or an ester group, and n1 is 0 or 1; or

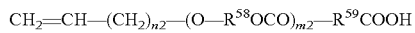

wherein $R^{58}$ and $R^{59}$ are the same or different, and are each independently a saturated or unsaturated linear or cyclic alkyl group, n2 is 0 or 1, and m2 is 0 or 1.

Specific examples of the carboxyl group-containing monomer unit include one or two or more selected from acrylic acid, methacrylic acid, vinylacetic acid, crotonic acid, cinnamic acid, 3-allyloxypropionic acid, itaconic acid, an itaconic acid monoester, maleic acid, a maleic acid monoester, maleic anhydride, fumaric acid, a fumaric acid monoester, vinyl phthalate, and vinyl pyromelliticate, and, in particular, preferable are crotonic acid, itaconic acid, maleic acid, a maleic acid monoester, fumaric acid, a fumaric acid monoester, and 3-allyloxypropionic acid, the homopolymerizablity of which is low.

The lower limit of the proportion of the carboxyl group-containing monomer unit is 0.1 mol % and preferably 0.4 mol %, and the upper limit is 2.0 mol % and preferably 1.5 mol %.

Specific examples of the hydroxyl group-containing fluorine-containing copolymer include:

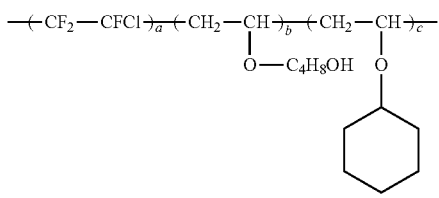

wherein the ratio of a, b, and c in terms of a molar ratio is a:b:c=40 to 60:3 to 15:5 to 45);

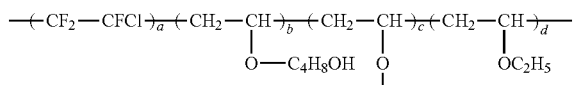

wherein the ratio of a, b, c, and d in terms of a molar ratio is a:b:c:d=40 to 60:3 to 15:5 to 45:5 to 45;

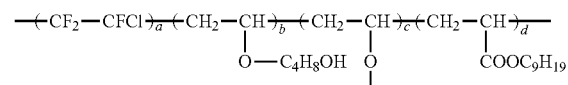

wherein the ratio of a, b, c, and d in terms of a molar ratio is a:b:c:d=40 to 60:3 to 15:5 to 45:5 to 45;

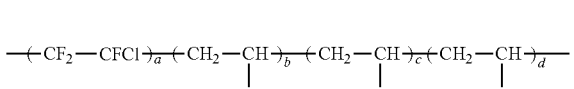

wherein the ratio of a, b, c, and d in terms of a molar ratio is a:b:c:d=40 to 60:3 to 15:5 to 45:5 to 45, and i-Bu means an isobutyl group; tetrafluoroethylene/vinyl versatate/hydroxybutyl vinyl ether; tetrafluoroethylene/vinyl versatate/hydroxyethyl vinyl ether/vinyl tert-butylbenzoate; tetrafluoroethylene/vinyl versatate/hydroxybutyl vinyl ether/crotonic acid; and tetrafluoroethylene/vinyl versatate/hydroxyethyl vinyl ether/vinyl benzoate/crotonic acid.

Examples of the fluoroelastomer include non-perfluoro fluoroelastomer and perfluoro fluoroelastomer.

Examples of the non-perfluoro fluoroelastomer include vinylidene fluoride (VDF) fluoroelastomer, tetrafluoroethylene (TFE)/propylene (Pr) fluoroelastomer, tetrafluoroethylene (TFE)/propylene/vinylidene fluoride (VDF) fluoroelastomer, ethylene/hexafluoropropylene (HFP) fluoroelastomer, ethylene/hexafluoropropylene (HFP)/vinylidene fluoride (VDF) fluoroelastomer, ethylene/hexafluoropropylene (HFP)/tetrafluoroethylene (TFE) fluoroelastomer, fluorosilicone fluoroelastomer, and fluorophosphazene fluoroelastomer, and these can be used singly or in any combination as long as the effects of the present disclosure are not impaired. In particular, vinylidene fluoride fluoroelastomer and tetrafluoroethylene/propylene fluoroelastomer are preferable.

The vinylidene fluoride fluoroelastomer refers to a fluorine-containing elastic copolymer composed of 45 to 85 mol % of vinylidene fluoride and 55 to 15 mol % of at least one further monomer copolymerizable with vinylidene fluoride. Preferably, it refers to a fluorine-containing elastic copolymer composed of 50 to 80 mol % of vinylidene fluoride and 50 to 20 mol % of at least one further monomer copolymerizable with vinylidene fluoride.

Examples of the at least one further monomer copolymerizable with vinylidene fluoride include fluorine-containing monomers such as tetrafluoroethylene (TFE), chlorotrifluoroethylene (CTFE), trifluoroethylene, hexafluoropropylene (HFP), trifluoropropylene, tetrafluoropropylene, pentafluoropropylene, trifluorobutene, tetrafluoroisobutene, perfluoro(alkyl vinyl ether) (PAVE), and vinyl fluoride, and fluorine-free monomers such as ethylene, propylene, and alkyl vinyl ether. These can be used singly or in any combination. Among these, tetrafluoroethylene, hexafluoropropylene, and perfluoro(alkyl vinyl ether) are preferably used.

Examples of perfluoro(alkyl vinyl ether) in this case include perfluoro(methyl vinyl ether) and perfluoro(propyl vinyl ether), and these can be used singly or in any combination as long as the effects of the present disclosure are not impaired.

Specific examples of the vinylidene fluoride fluoroelastomer include VDF-HFP rubber, VDF-HFP-TFE rubber, VDF-CTFE rubber, and VDF-CTFE-TFE rubber.

The tetrafluoroethylene/propylene fluoroelastomer refers to a fluorine-containing elastic copolymer composed of 45 to 70 mol % of tetrafluoroethylene, 55 to 30 mol % of propylene, and 0 to 5 mol % of a crosslinking site-providing monomer.

Examples of the crosslinking site-providing monomer include iodine-containing monomers such as perfluoro(6,6-dihydro-6-iodo-3-oxa-1-hexene) and perfluoro(5-iodo-3-oxa-1-pentene) as described in Japanese Patent Publication No. 5-63482 and Japanese Patent Laid-Open No. 7-316234, bromine-containing monomers described in Japanese Translation of PCT International Application Publication No. 1992-505341, and nitrile group-containing monomers, carboxyl group-containing monomers, and alkoxycarbonyl group-containing monomers as described in Japanese Translation of PCT International Application Publication No. 1992-505345 and Japanese Translation of PCT International Application Publication No. 1993-500070.

Examples of the perfluoro fluoroelastomer include TFE-containing perfluoroelastomer, such as a fluorine-containing elastic copolymer composed of TFE/perfluoro(alkyl vinyl ether) (PAVE)/a crosslinking site-providing monomer. The formulation thereof is preferably 45 to 90/10 to 50/0 to 5 (mol %), more preferably 45 to 80/20 to 50/0 to 5, and even more preferably 53 to 70/30 to 45/0 to 2. When outside of these formulation ranges, the perfluoro fluoroelastomer loses properties as a rubber elastic body and tends to have properties similar to a resin.

Examples of PAVE in this case include perfluoro(methyl vinyl ether) (PMVE) and perfluoro(propyl vinyl ether) (PPVE), and these may be used singly or in any combination as long as the effects of the present disclosure are not impaired.

Examples of the crosslinking site-providing monomer include iodine-containing monomers represented by the following formula:

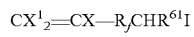
CX$^1_2$=CX—R$_f$CHR$^{61}$I wherein X$^1$ is H, F, or CH$_3$, R$_f$ is a fluoroalkylene group, a perfluoroalkylene group, a fluoropolyoxyalkylene group, or a perfluoropolyoxyalkylene group, and R$^{61}$ is H or CH$_3$; and monomers represented by the following formula:

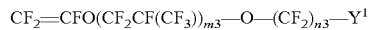
CF$_2$=CFO(CF$_2$CF(CF$_3$))$_{m3}$—O—(CF$_2$)$_{n3}$—Y$^1$ wherein m3 is an integer of 0 to 5, n3 is an integer of 1 to 3, and Y$^1$ is a nitrile group, a carboxyl group, an alkoxycarbonyl group, or a bromine atom, and these may be used singly or in any combination as long as the effects of the present disclosure are not impaired. The iodine atom, nitrile group, carboxyl group, alkoxycarbonyl group, and bromine atom thereof function as crosslinking points.

Specific examples of the perfluoro fluoroelastomer include fluoroelastomers described in International Publication No. WO 97/24381, Japanese Patent Publication No. 61-57324, Japanese Patent Publication No. 4-81608, Japanese Patent Publication No. 5-13961, and the like.

In addition, examples of the fluorine-containing polymer include homopolymers such as PVDF (polyvinylidene fluoride) and PVF (polyvinyl fluoride).

The reactive compatibilizer of the present disclosure can demonstrate its function merely by, in the step of mixing a fluorine-containing compound with a compound having reactivity with a nitrile oxide group by a mixer (such as a kneader, a Brabender, or an extruder) under normal pressure, mixing the reactive compatibilizer containing the compound of the present disclosure with these compounds. In such a mixing step, the compound of the present disclosure undergoes a click reaction with the reactive site of the compound having reactivity with a nitrile oxide group, and thus can introduce a fluorine-containing group into the compound having reactivity with a nitrile oxide group. The introduced fluorine-containing group has affinity for the fluorine-containing compound and thus enables both components to become compatible (become a composite).

The mixing step is usually carried out at a temperature at which the compound having reactivity with a nitrile oxide group and the fluorine-containing compound melt, e.g., about 150 to 250° C. For example, when NBR is used as the compound having reactivity with a nitrile oxide group, and PVDF is used as the fluorine-containing compound, the mixing step is carried out at about 170° C. or higher, e.g., about 180 to 210° C. The compound of the present disclosure is highly temperature-stable, and thus a treatment at such a high temperature is possible.

Moreover, the mixing step can be usually carried out without adding a solvent, an additive, and the like. However, according to the object, e.g., in order to accelerate the reaction, a solvent and an additive may be added. Those skilled in the art can select such a solvent and an additive according to the object.

Examples of compatibilizers commonly used to date include block polymers and graft polymers having the respective skeletons of the two components to be formed into a composite, and the compound of the present disclosure is advantageous by being more easily prepared than such polymers. Also, the reactive compatibilizer of the present disclosure is advantageous by being capable of compatibilizing the components to be formed into a composite merely by being mixed with a mixture of the components.

Moreover, the present disclosure provides a composite of two or more compounds treated with the reactive compatibilizer.

In one embodiment, the composition of the present disclosure is a cross-linking agent.

The cross-linking agent of the present disclosure contains at least one compound represented by the compound (I) of the present disclosure described above, and reacts with two functional groups having reactivity with a nitrile oxide group and thus makes it possible to cross-link the functional groups. The two functional groups may exist in the same molecule or may exist in different molecules, respectively.

The compound represented by the nitrile oxide compound (I) of the present disclosure has a higher thermal stability than conventional aromatic polyfunctional nitrile oxides, and thus can be used under high-temperature conditions. Accordingly, even when the compounds to be cross-linked are polymers wherein the number of reactive sites (i.e., unsaturated-bond sites) is small or polymers having poor molecular mobility because the main chain is rigid, the compounds can be cross-linked by treatment under high-temperature conditions. Specifically, even the polymers containing a fluorine-containing monomer as a main component, such as fluororesin, a fluoroelastomer base polymer, or a perfluororubber base polymer, can be suitably cross-linked.

The compound to be cross-linked is not limited as long as it has a site having reactivity with a nitrile oxide group, and may be, for example, a polymer that has a site having reactivity with a nitrile oxide group, such as general-purpose rubber, natural rubber, polynorbornene, and a fluoropolymer (preferably, a fluoropolymer obtained by polymerizing a fluoroolefin or a fluorine-containing (meth)acrylate, and particularly preferably a fluoroelastomer).

Examples of the general-purpose rubber include NBR (nitrile rubber), EPDM (ethylene-propylene-diene copolymer rubber), PAN (polyacrylonitrile), $H_2C=C(R^{62})-(CH_2-CHR^{62})_{n4}-CH_2-CR^{62}=CH_2$, wherein $R^{62}$ is each independently a hydrogen atom, a methyl group, an ethyl group, or an isobutyl group, and n4 is an integer of 10 to 1000).

Natural rubber is a rubbery polymer that usually occurs naturally and that usually has a polyisoprene structure, but is not limited thereto.

The fluorine-containing (meth)acrylate is a compound represented by $H_2C=C(X^2)-CO-O-Y^2$, wherein $X^2$ is any of a hydrogen atom, a methyl group, an ethyl group, a trifluoromethyl group, a fluorine atom, or a chlorine atom, and $Y^2$ is a linear or branched alkyl group having at least one fluoro group, preferably an alkyl group containing a perfluoroalkylene group or perfluoroalkyl group skeleton, and particularly preferably $-CH_2(CF_2)_nH$ or $-CH_2CH_2(CF_2)_nF$.

The fluoroelastomer may be any of non-perfluoro fluoroelastomer and perfluoro fluoroelastomer, and preferably contains a structural unit derived from at least one monomer selected from the group consisting of, for example, tetrafluoroethylene (TFE), vinylidene fluoride (VdF), and a perfluoro ethylenically unsaturated compound (such as hexafluoropropylene (HFP) or perfluoro(alkyl vinyl ether) (PAVE)) represented by the following formula (a):

wherein $Rf^a$ represents $-CF_3$ or $ORf^b$ ($Rf^b$ represents a perfluoroalkyl group having 1 to 5 carbon atoms).

Examples of the non-perfluoro fluoroelastomer include vinylidene fluoride (VdF) fluoroelastomer, tetrafluoroethylene (TFE)/propylene (Pr) fluoroelastomer, tetrafluoroethylene (TFE)/propylene (Pr)/vinylidene fluoride (VdF) fluoroelastomer, ethylene (Et)/hexafluoropropylene (HFP) fluoroelastomer, ethylene (Et)/hexafluoropropylene (HFP)/vinylidene fluoride (VdF) fluoroelastomer, ethylene (Et)/hexafluoropropylene (HFP)/tetrafluoroethylene (TFE) fluoroelastomer, fluorosilicone fluoroelastomer, and fluorophosphazene fluoroelastomer, and these can be used singly or in combinations. Also, these fluoroelastomers may be copolymers formed with a comonomer.

The comonomer is not limited as long as it is copolymerizable with another monomer, and examples include fluorine-containing monomers (c) such as TFE, HFP, PAVE, chlorotrifluoroethylene (CTFE), trifluoroethylene, trifluoropropylene, tetrafluoropropylene, pentafluoropropylene, trifluorobutene, tetrafluoroisobutene, hexafluoroisobutene, vinyl fluoride, iodine-containing fluorinated vinyl ether, and a fluorine-containing monomer represented by the following general formula (b):

wherein $Rf^b$ represents a linear or branched fluoroalkyl group having 1 to 12 carbon atoms; perfluorovinyl ethers represented by:

wherein $Rf^c$ represents a linear or branched perfluoroalkyl group having 1 to 6 carbon atoms, a cyclic perfluoroalkyl group having 5 to 6 carbon atoms, or a linear or branched perfluoroxyalkyl group having 2 to 6 carbon atoms and 1 to 3 oxygen atoms;

fluorine-free monomers such as ethylene (Et), propylene (Pr), and alkyl vinyl ether; and reactive emulsifiers. These can be used singly or in combinations of two or more.

Such a copolymers is not limited, and is, for example, at least one copolymer selected from the group consisting of a VdF/HFP copolymer, a VdF/TFE/HFP copolymer, a VdF/CTFE copolymer, a VdF/CTFE/TFE copolymer, a VdF/PAVE copolymer, a VdF/TFE/PAVE copolymer, a VdF/HFP/PAVE copolymer, a VdF/HFP/TFE/PAVE copolymer, a HFP/PAVE copolymer, a VdF/TFE/propylene (Pr) copolymer, a VdF/ethylene (Et)/HFP copolymer, and a copolymer of VdF/a fluorine-containing monomer (b) represented by formula (b).

The nitrile oxide group reactive moiety of the fluoroelastomer may be derived from a monomer having the reactive moiety, or may be a moiety reactive with a nitrile oxide group introduced by modifying a fluoroelastomer that does not have a reactive moiety.

Examples of the monomer having a moiety reactive with a nitrile oxide group include bis-olefin compounds such as bis-olefin compounds represented by the formula: $R^{22}R^{23}C=CR^{24}-Z^1-CR^{25}=CR^{26}R^{27}$ wherein $R^{22}$, $R^{23}$, $R^{24}$, $R^{25}$, $R^{26}$, and $R^{27}$ may be the same or different, and each represent a hydrogen atom or an alkyl group having 1 to 5 carbon atoms; and $Z^1$ represents a linear or branched alkylene or cycloalkylene group having 1 to 18 carbon atoms that may contain an oxygen atom and that is preferably at least partially fluorinated, or a (per)fluoroxyalkylene group.

Other examples of the monomer having a moiety reactive with a nitrile oxide group include olefin compounds having a nitrile group such as compounds represented by the formula: $R^{28}R^{29}C=CR^{30}-Z^2-CN$ (wherein $R^{28}$, $R^{29}$, and $R^{30}$ may be the same or different, and each represent a hydrogen atom or an alkyl group having 1 to 5 carbon atoms; and $Z^2$ represents a linear or branched alkylene or cycloalkylene group having 1 to 18 carbon atoms that may contain an oxygen atom and that is preferably at least partially fluorinated, or a (per)fluoroxyalkylene group), and a typical example is $CF_2=CFOCF_2CF(CF_3)OCF_2CF_2CN$.

Further examples of the monomer having a moiety reactive with a nitrile oxide group include acrylonitrile, 5-ethylidene-2-norbornene, and a styrene derivative having a nitrile group on an aromatic ring.

In one embodiment, the composition of the present disclosure is a fiber treatment agent.

The fiber treatment agent of the present disclosure contains at least one compound (I) of the present disclosure described above, and can increase the water- and oil-repellency and the like of a fiber having a group that has reactivity with a nitrile oxide group, such as an acrylic fiber.

The fiber treatment agent of the present disclosure can be suitably used on any fiber having a group that has reactivity with a nitrile oxide group.

Examples of such fibers include an acrylic fiber, and a polyester fiber or polyvinyl alcohol fiber obtained by copolymerizing a monomer having a nitrile group in a side chain. Even a fiber that does not have a group having reactivity with a nitrile oxide group can be treated with the fiber treatment agent of the present disclosure after introducing a group having reactivity with a nitrile oxide group. For example, the polyester fiber or polyvinyl alcohol fiber obtained by copolymerizing a monomer having a hydroxyl group or an amino group in a side chain can be treated with the fiber treatment agent of the present disclosure after being subjected to a dehydrative condensation reaction with a carboxylic acid or sulfonic acid compound having a group having reactivity with a nitrile oxide group.

The fiber treatment agent of the present disclosure may contain, in addition to the compound (I) of the present disclosure, additives such as an emulsifier (polyethylene glycol, cationic, ammonium, nonionic, or anionic), an antifoaming agent, a wetting agent, a paraffinic hydrocarbon, and the like.

The fiber treatment agent of the present disclosure may be applied to a fiber after being diluted with a solvent. Examples of the solvent include perfluoroaliphatic hydrocarbons having 5 to 12 carbon atoms (such as perfluorohexane, perfluoromethylcyclohexane, and perfluoro-1,3-dimethylcyclohexane); polyfluoroaromatic hydrocarbons (such as bis(trifluoromethyl)benzene); polyfluoroaliphatic hydrocarbons; hydrofluoroether (HFE) (for example, alkyl perfluoroalkyl ethers (the perfluoroalkyl group and the alkyl group may be linear or branched) such as perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF(OCH_3)C_3F_7$)), other fluorine-containing solvents, hydrocarbon solvents such as mineral oil, alcohols, MIRK (methyl isobutyl ketone), and glycol solvents (such as ethylene glycol and propylene glycol).

The method for applying the fiber treatment agent of the present disclosure to a fiber is not limited as long as the method causes the desired amount of the fiber treatment agent to be attached to the fiber, and various methods can be employed. Examples of the fiber treatment method include a continuous method and a batch method.

As for the continuous method, first, the fiber treatment agent is diluted with a solvent to prepare a treatment liquid. Next, a treatment target is continuously fed to an impregnating apparatus that is filled with the treatment liquid, the treatment target is impregnated with the treatment liquid, and then the unnecessary treatment liquid is removed. The impregnating apparatus is not limited, and a padder, a kiss roll-type applicator, a gravure coater-type applicator, a spray-type applicator, a foam-type applicator, a coating-type applicator, and the like can be preferably employed, and a padder is particularly preferable. Subsequently, a dryer is used to remove the solvent remaining in the treatment target. The dryer is not limited, and expansion dryers such as a hot flue and a tenter are preferable. The continuous method is preferably employed when the treatment target is a fabric such as a woven fabric.

The batch method includes the step of immersing the treatment target in a treating liquid and the step of removing the solvent remaining in the treated target. The batch method is preferably employed when the treatment target is not a fabric, such as bulk fiber, top, sliver, hank, tow, or thread, or when the treatment target is not suitable for the continuous method, such as a knitted fabric. In the immersion step, a cotton dyeing machine, a cheese dyeing machine, a jet dyeing machine, an industrial washing machine, a beam dyeing machine, and the like are usable. In the operation of removing the solvent, a hot air dryer such as a cheese dryer, a beam dryer or a tumble dryer, a high-frequency dryer, and the like are usable.

The treatment target to which the fiber treatment agent of the present invention is adhered is preferably subjected to a dry heat treatment. Performing a dry heat treatment is preferable because the active components in the fiber treatment agent more firmly adhere to the treatment target. The temperature of the dry heat treatment is preferably 120 to 180° C., and particularly preferably 160 to 180° C. The time of the dry heat treatment is preferably 10 seconds to 3 minutes, and particularly preferably 1 to 2 minutes. The method for the dry heat treatment is not limited, and a tenter is preferable when the treatment target is a fabric.

Moreover, the present disclosure provides a fiber that is treated with the fiber treatment agent.

The fiber treated with the fiber treatment agent of the present disclosure has, for example, increased water- and oil-repellency, weather resistance, and/or heat resistance according to the compound of the present disclosure used. The compound of the present disclosure chemically binds to the fiber by a click reaction, and thus the above functions are unlikely degraded by friction or the like and can be maintained for a long period of time.

While the present invention has been described in detail above, the present invention is not limited to these compounds and applications.

EXAMPLES

Synthesis Example 1

Introduction of Oxyethylene Chain into perfluoropolyether Terminal Alcohol

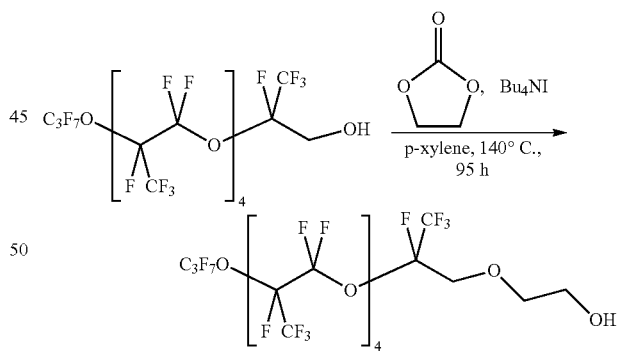

Ethylene carbonate (900 mg, 10.2 mmol), tetrabutylammonium iodide (40 mg, 0.11 mmol), and p-xylene were added to 1H,1H-perfluoro(2,5,8,11,14-pentamethyl-3,6,9,12,15-oxaoctadecan-1-ol) (5.0 g, 5.10 mmol), and the mixture was stirred at 140° C. for 95 hours. After the solvent was distilled off, the mixture was purified by silica gel column chromatography, and thus oxyethylene chain-introduced perfluoropolyether terminal alcohol (2.67 g, 2.61 mmol, 51.1%) was obtained as brown oil.

$^1$H NMR (500 MHz, 298 K, $(CD_3)_2CO$): δ4.16 (d, 2H, J=13 Hz, —C$\underline{H}_2$OCH$_2$CH$_2$O—), 3.83-3.71 (m, 4H, —CH$_2$OC$\underline{H}_2$CH$_2$O—, —CH$_2$OCH$_2$C$\underline{H}_2$O—).

Synthesis Example 2

Synthesis of perfluoropolyether Terminal Nitroalkane

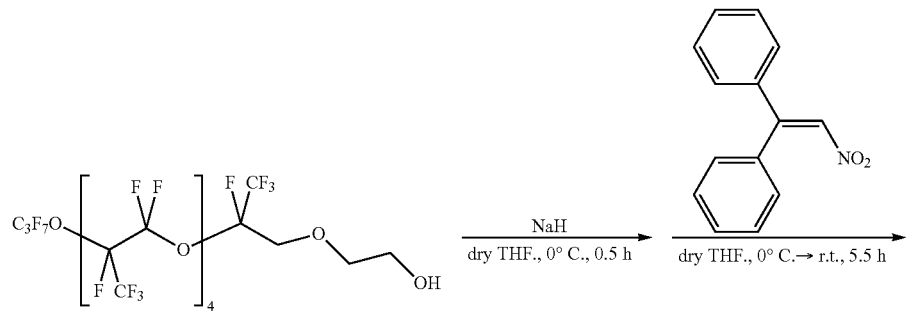

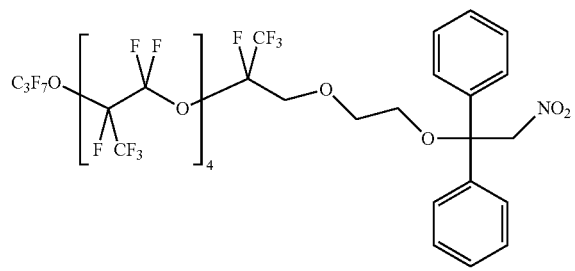

Sodium hydride (26 mg, 0.60 mmol) was sufficiently washed with hexane and purged with inert gas, and then dry tetrahydrofuran (THF, 1 ml) was added. Perfluoropolyether terminal alcohol (200 mg, 0.20 mmol) that was obtained in Synthesis Example 1 and that was dissolved in dry THF (0.5 mL) at 0° C. under ice cooling was added, the mixture was stirred for 30 minutes, diphenylnitroethene (88 mg, 0.40 mmol) dissolved in dry THF (0.5 ml) was added, and the mixture was stirred at room temperature for 5.5 hours. After quenching by adding a small amount of acetic acid and ion-exchanged water at 0° C., the mixture was sufficiently extracted with diethyl ether, and the resulting organic layer was washed with ion-exchanged water, a saturated aqueous sodium hydrogen carbonate solution, and saturated saline. The organic layer was dried over anhydrous magnesium sulfate and concentrated, then purified by silica gel column chromatography, and thereby perfluoropolyether terminal nitroalkane (128 mg, 0.10 mmol, 52.5%) as pale yellow oil was obtained.

$^1$H NMR (500 MHz, 298 K, CDCl$_3$): δ 7.36-7.27 (m, 6H, Ar), 7.28 (d, 4H, J=7.5 Hz, Ar), 5.35 (s, 2H, CH$_2$NO$_2$), 4.16 (d, 2H, J=13 Hz, —C$\underline{H}_2$OCH$_2$CH$_2$O—), 3.84 (t, 2H, J=4.5 Hz, —CH$_2$OC$\underline{H}_2$CH$_2$O—), 3.56 (br, 2H, —CH$_2$OCH$_2$C$\underline{H}_2$O—).

Example 1

Synthesis of perfluoropolyether Terminal Nitrile Oxide

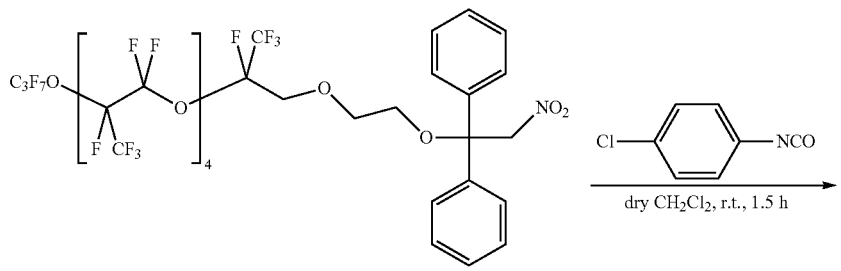

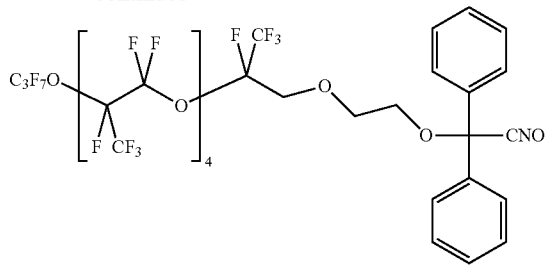

Dry dichloromethane (1 ml) and 4-chlorophenyl isocyanate (35 mg, 0.23 mmol) were added to perfluoropolyether terminal nitroalkane (128 mg, 0.10 mmol) obtained in Synthesis Example 2, the mixture was purged with inert gas, triethylamine (31 mg, 0.31 mmol) was added, and the mixture was stirred at room temperature for 1 hour and 30 minutes. After stirring was terminated, the precipitated insoluble matter was filtered off, and the filtrate was concentrated. Silica gel column chromatography was performed for purification, and thus nitrile-N-oxide (PEOE4-CNO, 88 mg, 0.07 mmol, 69.8%) was obtained as transparent oil.

$^1$H NMR (500 MHz, 298 K, CDCl$_3$): δ 7.45-7.42 (m, 4H, Ar), 7.41-7.35 (m, 6H, Ar), 4.13 (d, 2H, J=12 Hz, —CH$_2$OCH$_2$CH$_2$O—), 3.86 (t, 2H, J=4.0 Hz, —CH$_2$OC$\underline{H}_2$CH$_2$O—), 3.68 (t, 2H, J=4.0 Hz, —CH$_2$OCH$_2$C$\underline{H}_2$O—).

Example 2

Synthesis of Nitrile Oxide Derived from C$_6$F$_{13}$ Alcohol

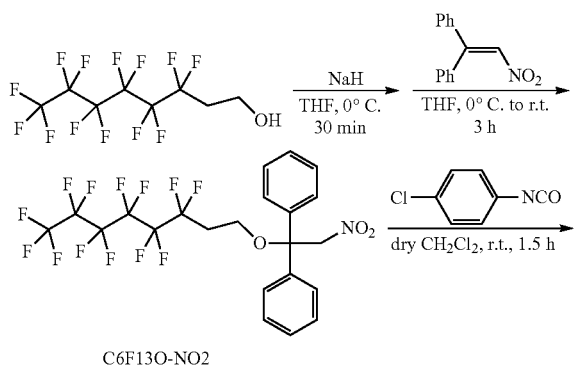

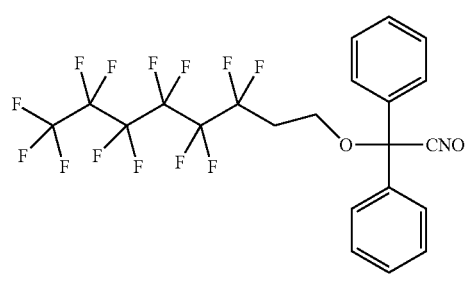

C6F13O-CNO

Synthesis of C$_6$F$_{13}$O—NO$_2$

In an Ar atmosphere, a THF solution (30 mL) of 1H,1H,2H,2H-tridecafluoro-1-n-octanol (1.0 g, 2.8 mmol) was added at 0° C. to a THF solution (30 mL) of hexane-washed sodium hydride (140 mg, 3.3 mmol). After the mixture was stirred for 30 minutes, a THF solution (30 mL) of diphenylnitroethene (740 mg, 3.3 mmol) was added, and the mixture was stirred at room temperature for 3 hours. Then, a small amount of acetic acid and ion-exchanged water were added at 0° C., and the mixture was dissolved in ethyl acetate, followed by quenching with 1.0 M hydrochloric acid. The mixture was extracted 3 times with ethyl acetate, and the resulting organic layer was washed with ion-exchanged water, a saturated aqueous sodium hydrogen carbonate solution, and saturated saline. The organic layer was dried over anhydrous magnesium sulfate, the solvent was distilled off, silica gel column chromatography was performed for purification, and thus C$_6$F$_{13}$O—NO$_2$ (1.6 g, 2.8 mmol) was obtained as pale yellow oil.

$^1$H NMR (500 MHz, 298 K, CDCl$_3$): δ 7.40-7.32 (m, 6H, Ar), 7.28 (d, 4H, J=7.5 Hz, Ar), 5.38 (s, 2H, CH$_2$NO$_2$), 3.69 (t, 2H, J=7.0 Hz, —CF$_2$CH$_2$C$\underline{H}_2$O—), 2.56-2.46 (m, 2H, CF$_2$C$\underline{H}_2$CH$_2$O—).

Synthesis of C$_6$F$_{13}$O—CNO

In an Ar atmosphere, triethylamine (840 mg, 8.4 mmol) was added to a dichloromethane solution (30 mL) of C$_6$F$_{13}$O—NO$_2$ (1.6 g, 2.8 mmol) and 4-chlorophenyl isocyanate (940 mg, 6.1 mmol), and the mixture was stirred at room temperature for 90 minutes. After stirring, the precipitated insoluble matter was filtered off, and the filtrate was concentrated. This was purified by silica gel column chromatography (ethyl acetate/hexane=1/20), and thus C$_6$F$_{13}$O—CNO (1.5 g, 2.6 mmol) was obtained as colorless oil in a yield of 94%.

$^1$H NMR (500 MHz, 298 K, CDCl$_3$): δ 7.45-7.36 (m, 10H, Ar), 3.78 (t, 2H, J=6.0 Hz, —CF$_2$CH$_2$C$\underline{H}_2$O—) 2.58-2.48 (m, 2H, —CF$_2$C$\underline{H}_2$CH$_2$O—).

Example 3

Synthesis of Nitrile Oxide Derived from $C_8F_{17}$ thiol

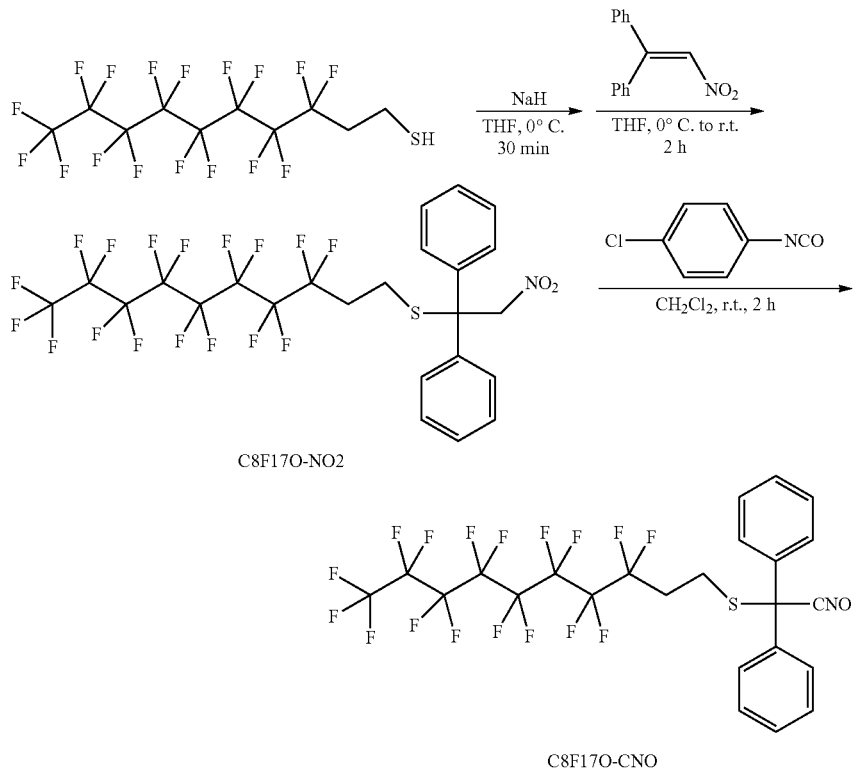

C8F17O-NO2

C8F17O-CNO

Synthesis of $C_8F_{17}S$—$NO_2$

In an Ar atmosphere, a THF solution (3 mL) of 1H,1H, 2H,2H-perfluorodecanethiol (100 mg, 0.21 mmol) was added at 0° C. to a THF solution (3 mL) of hexane-washed sodium hydride (13 mg, 0.31 mmol). After the mixture was stirred for 30 minutes, a THF solution (3 mL) of diphenylnitroethene (61 mg, 0.27 mmol) was added, and the mixture was stirred at room temperature for 2 hours. Then, a small amount of acetic acid and ion-exchanged water were added at 0° C., and the mixture was dissolved in ethyl acetate, followed by quenching with 1.0 M hydrochloric acid. The mixture was extracted 3 times with ethyl acetate, and the resulting organic layer was washed with ion-exchanged water, a saturated aqueous sodium hydrogen carbonate solution, and saturated saline. The organic layer was dried over anhydrous magnesium sulfate, the solvent was distilled off, silica gel column chromatography was performed for purification, and thus $C_8F_{17}S$—$NO_2$ (130 mg, 0.18 mmol) was obtained as pale yellow oil in a yield of 86%.

$^1$H NMR (500 MHz, 298 K, CDCl$_3$): δ 7.33-7.43 (m, 10H, Ar), 5.36 (s, 2H, CH$_2$NO$_2$), 2.48 (t, 2H, J=8.0 Hz, —CF$_2$CH$_2$CH$_2$S—), 1.97-1.86 (m, 2H, —CF$_2$C$\underline{H}_2$CH$_2$S—).

Synthesis of $C_8F_{17}S$—CNO

In an Ar atmosphere, triethylamine (29 mg, 0.29 mmol) was added to a dichloromethane solution (1.0 mL) of $C_8F_{17}S$—$NO_2$ (69 mg, 0.10 mmol) and 4-chlorophenyl isocyanate (30 mg, 0.19 mmol), and the mixture was stirred at room temperature for 2 hours. After stirring, the precipitated insoluble matter was filtered off, and the filtrate was concentrated. Dichloromethane was added again to the concentrated filtrate, and the precipitated insoluble matter was filtered off. This step was repeated twice, then the solvent was distilled off, silica gel column chromatography (chloroform/hexane=1/2) was performed for purification, and thus $C_8F_{17}S$—CNO (50 mg, 0.07 mmol) was obtained in a yield of 75% as colorless oil.

$^1$H NMR (500 MHz, 298 K, CDCl$_3$): δ 7.56-7.53 (m, 4H, Ar), 7.45-7.32 (m, 6H, Ar), 2.84 (t, 2H, J=8.0 Hz, CF$_2$CH$_2$C$\underline{H}_2$S—), 2.30-2.21 (m, 2H, —CF$_2$C$\underline{H}_2$CH$_2$S—).

Example 6

Surface Treatment (Coating)

Nitrile oxide obtained in Example 1 was applied to an allyl-modified glass plate (length 3 cm×width 2.6 cm) with a spatula, and heated at 70° C. for 14 hours and 30 minutes using a hot plate. After being cooled to room temperature, the glass plate was ultrasonically cleaned with 70 ml of chloroform 3 times and dried with cool air from a dryer. The contact angle of the surface before and after the treatment was measured, and the results are shown in the table below.

Example 7

Surface Treatment (Coating)

Nitrile oxide obtained in Example 2 was applied to an allyl-modified glass plate (length 3 cm×width 2.6 cm) with a spatula, and heated at 70° C. for 14 hours and 30 minutes using a hot plate. After being cooled to room temperature, the glass plate was ultrasonically cleaned with 70 ml of chloroform 3 times and dried with cool air from a dryer. The contact angle of the surface before and after the treatment was measured, and the results are shown in the table below.

Example 8

Surface Treatment (Immersion)

An allyl-modified glass plate (length 3 cm×width 2.6 cm) was immersed in a solution in which nitrile oxide (0.15 mmol) obtained in Example 1 was added to toluene (30 ml), and heated at 70° C. for 14 hours and 30 minutes using an oil bath. After being cooled to room temperature, the glass plate was ultrasonically cleaned with chloroform (50 ml) 3 times and dried with cool air from a dryer. The contact angle of the surface before and after the treatment was measured, and the results are shown in the table below.

TABLE 1

|  | Contact angle | |
| --- | --- | --- |
|  | Before treatment | After treatment |
| Example 6 | 61° | 111° |
| Example 7 | 66° | 102° |
| Example 8 | 56° | 97° |

INDUSTRIAL APPLICABILITY

The compound of the present disclosure is suitably used in a variety of applications, for example, as a surface-treating agent.

The invention claimed is:

1. A compound represented by formula (I):

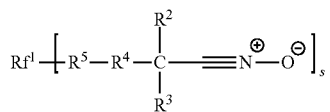

wherein
Rf$^1$ is a monovalent or divalent perfluoropolyether group;
R$^2$ and R$^3$ are each independently at each occurrence a hydrogen atom or a hydrocarbon group;
R$^4$ is each independently at each occurrence —S—, —NR$^7$—, or —O—P(═O) (OR$^8$)—;
R$^5$ is each independently at each occurrence:

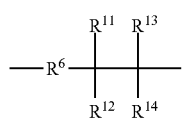

wherein
R$^6$ is a divalent organic group;
R$^{11}$ is a hydrogen atom or an alkyl group having 1 to 6 carbon atoms;
R$^{12}$ is a hydrogen atom or an alkyl group having 1 to 6 carbon atoms;
R$^{13}$ is a hydrogen atom or an alkyl group having 1 to 6 carbon atoms; and
R$^{14}$ is a hydrogen atom or an alkyl group having 1 to 6 carbon atoms;
R$^7$ is each independently at each occurrence a hydrogen atom or a hydrocarbon group;
R$^8$ is each independently at each occurrence a hydrocarbon group; and
s is 1 or 2.

2. The compound according to claim 1, wherein R$^4$ is —S—.

3. The compound according to claim 1, wherein R$^6$ is an alkylene group, or an alkyleneoxy group.

4. A compound represented by formula (II):

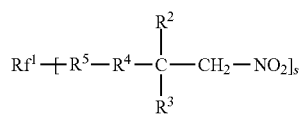

wherein
Rf$^1$ is a monovalent or divalent perfluoropolyether group;
R$^2$ and R$^3$ each independently at each occurrence is a hydrogen atom or a hydrocarbon group;
R$^4$ is each independently at each occurrence —S—, —NR$^7$—, or —O—P(═O) (OR$^8$)—;
R$^5$ is each independently at each occurrence:

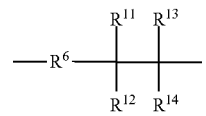

wherein
R$^6$ is a divalent organic group;
R$^{11}$ is a hydrogen atom or an alkyl group having 1 to 6 carbon atoms;
R$^{12}$ is a hydrogen atom or an alkyl group having 1 to 6 carbon atoms;
R$^{13}$ is a hydrogen atom or an alkyl group having 1 to 6 carbon atoms; and
R$^{14}$ is a hydrogen atom or an alkyl group having 1 to 6 carbon atoms;
R$^7$ is each independently at each occurrence a hydrogen atom or a hydrocarbon group;
R$^8$ is each independently at each occurrence a hydrocarbon group; and
s is 1 or 2.

5. A composition comprising one or more compounds according to claim 1 for being applied to a material comprising a group having reactivity with a nitrile oxide group.

6. A compound represented by formula (I):

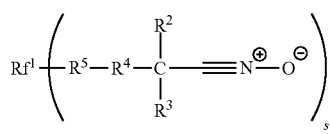

wherein
Rf$^1$ is a monovalent or divalent perfluoropolyether group;
R$^2$ and R$^3$ are each independently at each occurrence a hydrogen atom or a hydrocarbon group;
R$^4$ is —O—;

$R^5$ is each independently at each occurrence:

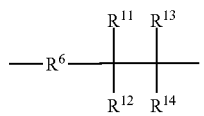

wherein
$R^6$ is
 —$R^{16}$—
 —$R^{16'}$—$R^{18}$—, or
 —$R^{16}$—$R^{18}$—$R^{16}$—
wherein
$R^{16}$ is an alkylene group having 1 to 20 carbon atoms,
$R^{16'}$ is a branched alkylene group having 3 to 20 carbon atoms, and
$R^{18}$ is an oxygen atom;
$R^{11}$ is a hydrogen atom or an alkyl group having 1 to 6 carbon atoms;
$R^{12}$ is a hydrogen atom or an alkyl group having 1 to 6 carbon atoms;
$R^{13}$ is a hydrogen atom or an alkyl group having 1 to 6 carbon atoms; and
$R^{14}$ is a hydrogen atom or an alkyl group having 1 to 6 carbon atoms;
and
s is 1 or 2.

7. A compound represented by formula (II):

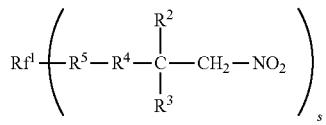

wherein
$Rf^1$ is a monovalent or divalent perfluoropolyether group;
$R^2$ and $R^3$ each independently at each occurrence is a hydrogen atom or a hydrocarbon group;
$R^4$ is —O—;
$R^5$ is each independently at each occurrence:

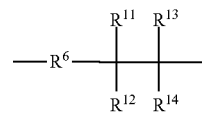

wherein
$R^6$ is
 —$R^{16}$—
 —$R^{16'}$—$R^{18}$—, or
 $R^{16}$—$R^{18}$—$R^{16}$—
wherein
$R^{16}$ is an alkylene group having 1 to 20 carbon atoms,
$R^{16'}$ is a branched alkylene group having 3 to 20 carbon atoms, and
$R^{18}$ is an oxygen atom;
$R^{11}$ is a hydrogen atom or an alkyl group having 1 to 6 carbon atoms;
$R^{12}$ is a hydrogen atom or an alkyl group having 1 to 6 carbon atoms;
$R^{13}$ is a hydrogen atom or an alkyl group having 1 to 6 carbon atoms; and
$R^{14}$ is a hydrogen atom or an alkyl group having 1 to 6 carbon atoms;
and
s is 1 or 2.

\* \* \* \* \*